United States Patent [19]

Takayanagi et al.

[11] Patent Number: 5,612,303

[45] Date of Patent: Mar. 18, 1997

[54] SOLVENT COMPOSITION

[75] Inventors: Yasuyuki Takayanagi; Satoshi Endou; Naoki Sugama, all of Kanagawa, Japan

[73] Assignee: Nitto Chemical Industry Co., Ltd., Tokyo, Japan

[21] Appl. No.: 555,309

[22] Filed: Nov. 8, 1995

Related U.S. Application Data

[63] Continuation-in-part of Ser. No. 260,741, Jun. 15, 1994, abandoned.

[30] Foreign Application Priority Data

| Jun. 15, 1993 | [JP] | Japan | 5-167374 |
| Jun. 22, 1993 | [JP] | Japan | 5-173606 |
| Sep. 19, 1993 | [JP] | Japan | 5-253688 |
| Dec. 24, 1993 | [JP] | Japan | 5-346056 |
| Mar. 11, 1994 | [JP] | Japan | 6-103457 |

[51] Int. Cl.$^6$ ................................. C11D 7/22

[52] U.S. Cl. .................. 510/174; 510/175; 510/176; 510/243; 510/245; 510/364; 510/365; 510/407

[58] Field of Search ......................... 510/174, 175, 510/176, 243, 245, 364, 365, 407

[56] References Cited

U.S. PATENT DOCUMENTS

| 3,336,234 | 8/1967 | Speight | 252/171 |
| 3,368,943 | 2/1968 | Gilbert | 167/94 |
| 5,053,535 | 10/1991 | Shima et al. | 562/579 |
| 5,068,051 | 11/1991 | Kikuchi et al. | 252/162 |
| 5,128,230 | 7/1992 | Templeton et al. | 430/191 |

FOREIGN PATENT DOCUMENTS

| 0429800A2 | 4/1990 | European Pat. Off. | C07C 69/54 |
| 54-092635 | 7/1979 | Japan . | |
| 1132694 | 5/1989 | Japan | C11D 7/50 |
| 341170 | 2/1991 | Japan | C09D 9/00 |
| 3167298 | 7/1991 | Japan | C11D 7/50 |
| 3284651 | 12/1991 | Japan | C07C 69/708 |
| 459984 | 2/1992 | Japan | C23G 5/02 |
| 459985 | 2/1992 | Japan | C23G 5/02 |
| 468092 | 3/1992 | Japan | C11D 10/02 |
| 468094 | 3/1992 | Japan | C11D 10/02 |
| 468088 | 3/1992 | Japan | C11D 7/26 |
| 468090 | 3/1992 | Japan | C11D 7/60 |

Primary Examiner—Margaret Einsmann
Attorney, Agent, or Firm—Sughrue, Mion, Zinn, Macpeak & Seas

[57] ABSTRACT

A solvent composition containing at least one of an alkyl α-alkoxyisobutyrate, an alkyl β-alkoxyisobutyrate, and an alkyl α-hydroxyisobutyrate as an active component is disclosed. The solvent composition is of low toxicity and harmless to humans, has an extremely high dissolving power for high polymers, fats and oils, fluxes, liquid crystals, etc., produces no environment destructive substance, gives off no offensive odor, and has a relatively high boiling point indicative of safety and ease in handling.

26 Claims, No Drawings

SOLVENT COMPOSITION

This is a Continuation-In-Part of application Ser. No. 08/260,741, filed on Jun. 15, 1994 now abandoned.

FIELD OF THE INVENTION

This invention relates to a solvent composition, and more particularly to a solvent composition suitable for use as a solvent or an assistant in paints and varnishes, coatings, adhesives, printing inks, cleaning agents, agricultural chemicals, and cosmetics.

BACKGROUND OF THE INVENTION

Solvents have played an important roll in the development of the chemical industry. In particular, the importance of solvents in the fields of coating compositions, adhesives and printing inks has been ever increasing, with the recent remarkable development in the plastics industry. Coating compositions, adhesives, printing inks, etc. are generally used in the form of a solution in a solvent for assuring ease in handling on use, and for uniformly and intimately applying a high polymer base to a substrate. To this effect, it is very important for the solvent to have moderate volatility, while retaining sufficient dissolving power for the high polymer base and uniform coating properties, as well as ease in handling. In other words, the quality of coating compositions, adhesives, and printing inks largely depends on the choice of solvent.

Glycol ether type cellosolves, especially Cellosolve acetate (ethylene glycol monoethyl ether acetate), have been used for their excellent properties as solvents for cellulose resins, epoxy resins, acrylic resins, vinyl resins (e.g., vinyl acetate resins and vinyl chloride resins), alkyd resins, and polyester resins which are commonly used in the fields of coating compositions, adhesives and printing inks. In recent years, however, demand for safety of chemical substances has been increasing from the standpoint of environmental pollution. In this regard, use of Cellosolve acetate is strictly limited because of its toxicity, and the Japanese Industrial Safety and Health Law laid down criteria for controlling the working environment concentration thereof.

Intensive studies have therefore been directed to development of a solvent which can be a satisfactory substitute for Cellosolve acetate in terms of dissolving power, and yet gives rise to no safety problem. For example, ethyl lactate, propylene glycol monomethyl ether acetate, methoxypropanol, and ethyl β-ethoxypropionate have been studied as promising alternatives. However, they are not always satisfactory in dissolving power, safety, smell, and ease in handling. Of these alternative solvents, ethyl lactate, which is permitted as a food additive, seems the most preferred from the standpoint of safety, but it is not deemed to have sufficient dissolving power for high polymers and various additives. While alkyl β-alkoxypropionates, such as methyl β-methoxypropionate and ethyl β-ethoxypropionate, appear to be the most preferred from the viewpoint of dissolving power, they are still unsatisfactory in terms of dissolving power for high polymers or various additives, and in volatility after application. A mixture of methyl β-methoxypropionate and ethyl β-ethoxypropionate has been proposed as a solvent with improved physical properties, as disclosed in JP-A-3-284651 (the term "JP-A" as used herein means an "unexamined published Japanese patent application"). However, preparation of mixture involves a complicated operation, and is not suitable for industrial use. Thus, a practical solvent equal to Cellosolve acetate in performance has not yet been developed.

Besides the aforementioned applications, solvents are used in cleaning agents for removing oils, such as cutting oil, process oil, anti-corrosive oil, lubricating oil, grease and pitch, solder fluxes, inks, and liquid crystals.

Solvent-solubility of inks widely varies depending on their kind, for example, the kind of the base polymer or the hardening mechanism, such as ultraviolet-curing, heat-curing or hardening by evaporation. Therefore, an ink remover is must have a strong dissolving power to be applicable to any kind of ink.

In the production of liquid crystal displays, it is necessary to form a high-density electrode pattern on a glass substrate so as to make a fine display. However, it is not easy to keep dense lines of an electrode pattern insulated from each other. Existence of even a trace amount of a contaminant on the substrate causes display defects due to insufficient insulation or burnout due to continuous galvanic corrosion. This ultimately results in destruction of the display function. In particular, when a liquid crystal is injected into a liquid crystal cell, the liquid crystal adheres to unnecessary parts of the cell through capillary action. The adhered unnecessary liquid crystal, if left as such, will fail to provide a clear display image, and also contaminants in the air are taken up by dissolution, which tends to cause insufficient insulation. Therefore, the adhered unnecessary liquid crystal must be removed with a cell cleaner, but it is very difficult to completely remove the liquid crystal which has entered narrow gaps.

For these uses, solvents mainly comprising halogen type solvents, such as Freon 113 (1,1,2-trichloro-1,2,2-trifluoroethane), methyl chloroform (1,1,1-trichloroethane), and trichloroethylene, have been in wide use. In particular, Freon 113 has been used extensively because of its nonflammability, low toxicity, excellent stability, and dissolving power selective for various kinds of contaminants with no corrosion of metals, plastics or elastomers. However, because Freon 113 and methyl chloroform rise up to the stratosphere and destroy the ozonosphere, which eventually leads to induction of cancer of skin, their use has been severely restricted. Use of trichloroethylene is also now been restricted because it is suspected as being carcinogenic.

Accordingly, intensive studies have been conducted in order to secure a cleaning agent which will take the place of Freons, showing a cleaning action equal to the Freon 113, without entertaining a fear of destruction of the ozonosphere. For example, a number of substitutes for Freons have been proposed to date, including a composition mainly comprising 1,2-difluoroethane (see JP-A-1-132694), a mixture of 1,1-dichloro-2,2,2-trifluoroethane and dimethoxymethane (see JP-A-2-178396, corresponding to U.S. Pat. No. 5,068,051), and a composition mainly comprising hexafluorobenzene (see JP-A-3-167298). However, none of these solvent compositions offers a complete solution to the above-mentioned problems, i.e., they do not compare with Freon 113 in terms of performance. In addition, there is a movement to restrict use of these halogen type solvents.

On the other hand, cleaning agents for removal of fats and oils, i.e., degreasing agents, which are highly safe to humans and which do not cause environmental destruction have been proposed. For example, a composition mainly comprising a nonionic surface active agent and an alkyl lactate (see JP-A-4-68088), a composition mainly comprising a nonionic surface active agent and an adipic ester (see JP-A-4-

59985), a composition mainly comprising a nonionic surface active agent and a polyalkylene glycol dialkyl ether (see JP-A- 4-59984), a composition mainly comprising a nonionic surface active agent and N-methylpyrrolidone, etc. (see JP-A-4-68094), a composition mainly comprising a nonionic surface active agent and a glycerin acetate compound (see JP-A-4-68092), and a composition mainly comprising an alcohol and a fatty acid ester (see JP-A-4-68090) have been proposed. Although an alkyl lactate, N-methylpyrrolidone, etc. are highly safe solvents in terms of low toxicity, and do not cause environmental destruction or accumulate in the environment, they have insufficient dissolving power for fats and oils when used alone, as is obvious from the Comparative Examples given in the aforementioned patent publications. They essentially need a combined use of a detergent aid, such as a surface active agent, for application as a degreasing agent.

A solvent composition mainly comprising an alkyl lactate which is highly safe to humans and does not cause environmental destruction has been proposed as a cleaning agent for removing inks, i.e., an ink remover, as disclosed in JP-A-3-41170. While an alkyl lactate is a highly safe solvent in terms of low toxicity, and does not cause environmental destruction or accumulate in the environment, it is still unsatisfactory as an ink remover due to insufficient dissolving power for high polymer-based inks.

As discussed above, it has been desired in the art to develop a solvent system which substitutes for Cellosolve acetate, Freon 113, methyl chloroform, etc., while exhibiting a high dissolving power for high polymers, fats and oils, solder fluxes, liquid crystals, agricultural chemicals, cosmetics, and various compounding additives, without giving rise to safety problems.

SUMMARY OF THE INVENTION

An object of the present invention is to provide a solvent composition freed of the drawbacks of conventional solvents, such as Cellosolve acetate, Freon 113 and methyl chloroform, comprising a solvent system which is of low toxicity and harmless to humans, has high dissolving power, does not produce environment destructive substances, does not give off offensive odor, and has a relatively high boiling point indicative of safety and ease in handling.

As a result of extensive research into a solvent composition having the above-described favorable properties, the present inventors have found that the object of the present invention can be met by an oxyisobutyric acid ester selected from an alkyl α-alkoxyisobutyrate, alkyl β-alkoxyisobutyrate, and alkyl α-hydroxyisobutyrate. The present invention has been completed based on this finding.

The present invention provides a solvent composition containing, as an active component, at least one oxyisobutyric acid ester selected from the group consisting of an alkyl α-alkoxyisobutyrate represented by formula (I):

an alkyl β-alkoxyisobutyrate represented by formula (II):

and an alkyl α-hydroxyisobutyrate represented by formula (III):

wherein $R^1$ and $R^2$ each represent ah alkyl group having from 1 to 4 carbon atoms.

DETAILED DESCRIPTION OF THE INVENTION

The oxyisobutyric acid esters represented by formulae (I), (II) and (III), which can be used in the present invention, are available as disclosed, for example, in EP-A-429800.

The solvent composition of the present invention essentially contains an alkyl oxyisobutyrate. The alkyl oxyisobutyrates include alkyl α-alkoxyisobutyrates (I), such as methyl α-methoxyisobutyrate, ethyl α-methoxyisobutyrate, methyl α-ethoxyisobutyrate, and ethyl α-ethoxyisobutyrate; alkyl α-alkoxyisobutyrates (II), such as methyl β-methoxyisobutyrate, ethyl β-methoxyisobutyrate, methyl β-ethoxyisobutyrate, ethyl β-ethoxyisobutyrate, methyl β-isopropoxyisobutyrate, ethyl β-isopropoxyisobutyrate isopropyl β-isopropoxyisobutyrate, butyl β-isopropoxyisobutyrate, methyl β-butoxyisobutyrate, ethyl β-butoxyisobutyrate, and butyl β-butoxyisobutyrate; and alkyl α-hydroxyisobutyrates (III), such as methyl α-hydroxyisobutyrate, ethyl α-hydroxyisobutyrate, isopropyl α-hydroxyisobutyrate, and butyl α-hydroxyisobutyrate. From the standpoint of dissolving power and volatility, methyl α-methoxyisobutyrate, ethyl α-ethoxyisobutyrate, methyl β-methoxyisobutyrate, ethyl β-methoxyisobutyrate, methyl β-ethoxyisobutyrate, ethyl β-ethoxyisobutyrate, methyl β-isopropoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, isopropyl α-hydroxyisobutyrate, and butyl α-hydroxyisobutyrate, are preferred.

The solvent composition of the present invention is also useful as a degreasing agent, an ink remover, a flux remover, a liquid crystal cell cleaner or a resist stripper.

Alkyl oxyisobutyrates which are particularly useful as a degreasing agent include methyl α-methoxyisobutyrate, ethyl α-ethoxyisobutyrate, methyl β-methoxyisobutyrate, methyl β-ethoxyisobutyrate, ethyl β-ethoxyisobutyrate, methyl β-isopropoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, isopropyl α-hydroxyisobutyrate, and butyl α-hydroxyisobutyrate.

Alkyl oxyisobutyrates which are particularly useful as an ink remover include methyl α-methoxyisobutyrate, methyl β-methoxyisobutyrate, ethyl β-methoxyisobutyrate, methyl β-ethoxyisobutyrate, ethyl β-ethoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, and butyl α-hydroxyisobutyrate.

Alkyl oxyisobutyrates which are particularly useful as a flux remover include methyl α-methoxyisobutyrate, ethyl α-ethoxyisobutyrate, methyl β-methoxyisobutyrate, ethyl β-methoxyisobutyrate, methyl β-ethoxyisobutyrate, ethyl β-ethoxyisobutyrate, methyl β-isopropoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, isopropyl α-hydroxyisobutyrate, and butyl α-hydroxyisobutyrate.

Alkyl oxyisobutyrates which are particularly useful as a liquid crystal cell cleanser include methyl α-methoxyisobutyrate, methyl β-methoxyisobutyrate, ethyl β-methoxyisobutyrate, methyl β-ethoxyisobutyrate, ethyl β-ethoxyisobutyrate, methyl β-isopropoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, and butyl α-hydroxyisobutyrate.

Alkyl oxyisobutyrates which are particularly useful as a resist stripper include methyl α-methoxyisobutyrate, ethyl α-ethoxyisobutyrate, methyl β-methoxyisobutyrate, ethyl β-methoxyisobutyrate, methyl β-ethoxyisobutyrate, ethyl β-ethoxyisobutyrate, methyl β-isopropoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, isopropyl α-hydroxyisobutyrate, and butyl α-hydroxyisobutyrate.

The alkyl α-alkoxyisobutyrates represented by formula (I), alkyl β-alkoxyisobutyrates represented by formula (II) and alkyl α-hydroxyisobutyrates represented by formula (III) may be used either individually or in combination of two or more thereof. While not limiting in combination, alkyl oxyisobutyrates represented by formula (I) or (II) is preferably used in combination with α-hydroxyisobutyrates represented by formula (III), in order to take advantage of dissolving power. The proportion of the alkyl oxyisobutyrates represented by formula (I) or (II)/α-hydroxyisobutyrates represented by formula (III) is preferably from 5/95 to 95/5 by weight, more preferably from 10/90 to 90/10 by weight, most preferably from 30/70 to 70/30 by weight.

The alkyl α-alkoxyisobutyrates, alkyl β-alkoxyisobutyrates, and alkyl α-hydroxyisobutyrates are compatible with other general organic solvents, such as alcohols, esters, ketones, amides, and aromatic hydrocarbons. They exhibit markedly excellent dissolving power for a wide range of organic compounds, e.g., polymeric compounds, which include natural resins, such as cellulose resins, and synthetic resins, such as epoxy resins, acrylic resins, vinyl resins (e.g., vinyl acetate resins and vinyl chloride resins), alkyd resins, polyester resins, novolak resins, polystyrene resins, phenoxy resins, phenoxy resins, polysulfone, methacrylate.styrene copolymer and acrylonitrile.styrene copolymer, as well as general hydrocarbon-based fats and oils, particularly polyester resins, polystyrene resins, acrylic resins, epoxy resins, phenoxy resins, polysulfone, methyl methacrylate.styrene copolymer and acrylonitrile.styrene copolymer. Accordingly, the oxyisobutyric esters of the present invention not only serve as a solvent by themselves, but they also exhibit excellent performance as a diluent or an auxiliary solvent for other organic solvents. Thus, they can be formulated into a solvent composition together with other organic solvents. While not limiting, the proportion of the oxyisobutyric ester in the solvent composition is preferably not less than 5% by weight, and more preferably not less than 10% by weight, in order to take full advantage of the safety and dissolving power of the oxyisobutyric ester.

The other solvents with which the oxyisobutyric esters of the present invention may be combined are not particularly limited and include water, alcohols, ethers, esters, ketones, amides, aliphatic hydrocarbons, and aromatic hydrocarbons. Suitable examples of the other solvents are water, methyl isobutyl carbinol, hexanol, heptanol, octanol, nonanol, 3-methylbutanol, propylene glycol, 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, tripropylene glycol monomethyl ether, tripropylene glycol monopropyl ether, tripropylene glycol monobutyl ether, propylene glycol dimethyl ether, dipropylene glycol dimethyl ether, tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone, methyl isoamyl ketone, acetophenone, propiophenone, benzophenone, cyclohexanone, isophorone, pyrrolidone, N-methylpyrrolidone, dimethylformamide, dimethylacetamide, dimethyl sulfoxide, sulfolane, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, methyl propionate, ethyl propionate, butyl propionate, benzyl propionate, methyl benzoate, ethyl benzoate, propyl benzoate, isoamyl benzoate, benzyl benzoate, diethyl ether, dipropyl ether, dibutyl ether, diphenyl ether, benzyl methyl ether, benzyl ethyl ether, anisole, phenetole, butyl phenyl ether, methoxytoluene, tetrahydrofuran, dibenzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol, methyl acetoacetate, ethyl acetoacetate, dimethyl maleate, dimethyl malonate, dimethyl succinate, dimethyl glutarate, dimethyl adipate, dimethyl phthalate methyl cinnamate, ethyl cinnamate, toluene, xylene, tetralin, decalin, limonene, and an aliphatic hydrocarbon having a boiling point of from 30° to 300° C. which is selected from the group consisting of a straight-chain paraffin, an isoparaffin and a cycloparaffin. Preferred of them are water, hexanol, heptanol, octanol, 3-methylbutanol, 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, tripropylene glycol monomethyl ether, tripropylene glycol monopropyl ether, propylene glycol dimethyl ether, dipropylene glycol dimethyl ether, tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone, methyl isoamyl ketone, acetophenone, propiophenone, cyclohexanone, N-methylpyrrolidone, dimethylformamide, dimethylacetamide, dimethyl sulfoxide, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, methyl propionate, ethyl propionate, butyl propionate, methyl benzoate, ethyl benzoate, propyl benzoate, isoamyl benzoate, diethyl ether, dipropyl ether, dibutyl ether, diphenyl ether, benzyl methyl ether, benzyl ethyl ether, anisole, methoxytoluene, tetrahydrofuran, dibenzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol, methyl acetoacetate, ethyl acetoacetate, dimethyl maleate, dimethyl malonate, dimethyl succinate, dimethyl glutarate, dimethyl adipate, dimethyl phthalate, toluene, xylene, tetralin, decalin, limonene, and an aliphatic hydrocarbon having a boiling point of from 30° to 300° C. which is selected from a straight-chain paraffin, an isoparaffin and a cycloparaffin, more preferably water, hexanol, 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, propylene glycol dimethyl ether, dipropylene glycol dimethyl ether, 2-ethyl-1-hexanol, cyclohexanol, benzyl alcohol, acetone, methyl ethyl ketone, methyl isobutyl ketone, methyl isoamyl ketone, acetophenone, propiophenone, cyclohexanone, N-methylpyrrolidone, dimethylformamide, dimethylacetamide, dimethyl sulfoxide, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, diethyl ether, dipropyl ether, dibutyl ether, diphenyl ether, tetrahydrofuran, dibenzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol, methyl acetoacetate, ethyl acetoacetate, toluene, xylene, tetralin, limonene, and an aliphatic hydrocarbon having a boiling point of from 30° to 300° C. which is selected from the group consisting of a straight-chain paraffin, an isoparaffin and a cycloparaffin.

Solvents which are particularly preferred to provide a degreasing agent include heptanol, octanol, 3-methylbutanol, 3-methoxybutanol, 3-methyl-3-methoxybutanol, 3,5,5-trimethyl-1-hexanol, 2-ethyl-1-hexanol, cyclohexanol, benzyl alcohol, acetone, methyl ethyl ketone, methyl isobutyl ketone, cyclohexanone, isophorone, N-methylpyrrolidone, dimethylformamide, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, dibenzyl ether, water, hexanol, heptanol, octanol, 3-methylbutanol, propylene glycol, 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, tripropylene glycol monomethyl ether, tripropylene glycol monopropyl ether, propylene glycol dimethyl ether, dipropylene glycol dimethyl ether, tripropylene glycol dimethyl ether, 3,5,5-trimethyl-1-hexanol, 2-ethyl-1-hexanol, cyclohexanol, benzyl alcohol, acetonic, methyl ethyl ketone, methyl isobutyl ketone, methyl isoamyl ketone, acetophenone, propiophenone, benzophenone, cyclohexanone, isophorone, pyrrolidone, N-methylpyrrolidone, dimethylformamide, dimethylacetamide, dimethyl sulfoxide, sulfolane, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, methyl propionate, ethyl propionate, butyl propionate, benzyl propionate, methyl benzoate, ethyl benzoate, propyl benzoate, isoamyl benzoate, benzyl benzoate, diethyl ether, dipropyl ether, dibutyl ether, diphenyl ether, benzyl methyl ether, benzyl ethyl ether, anisole, phenetole, butyl phenyl ether, methoxytoluene, tetrahydrofuran, dibenzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol, methyl acetoacetate, ethyl acetoacetate, dimethyl maleate, dimethyl malonate, dimethyl succinate, dimethyl glutarate, dimethyl adipate, dimethyl phthalate, toluene, xylene, tetralin, decalin, limonene, and an aliphatic hydrocarbon having a boiling point of from 30° to 300° C. which is selected from the group consisting of a straight-chain paraffin, an isoparaffin and a cycloparaffin.

Solvents which are particularly useful to provide an ink remover include water, methyl isobutyl carbinol, octanol, nonanol, 3-methylbutanol, propylene glycol, 3-methoxybutanol, 3-methyl-3-methoxybutanol, propylene glycol monomethyl ether, propylene glycol monopropyl ethers, propylene glycol monobutyl ether, dipropylene glycol monomethyl ether, dipropylene glycol monopropyl ether, dipropylene glycol monobutyl ether, tripropylene glycol monomethyl ether, tripropylene glycol monopropyl ether, tripropylene glycol monobutyl ether, propylene glycol dimethyl ether, dipropylene glycol dimethyl ether, tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone, methyl isoamyl ketone, acetophenone, propiophenone, benzophenone, cyclohexanone, isophorone, pyrrolidone, N-methylpyrrolidone, dimethylformamide, dimethylacetamide, dimethyl sulfoxide, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, methyl propionate, ethyl propionate, butyl propionate, benzyl propionate, methyl benzoate, ethyl benzoate, propyl benzoate, isoamyl benzoate, benzyl benzoate, diethyl ether, dipropyl ether, dibutyl ether, diphenyl ether, benzyl methyl ether, benzyl ethyl ether, anisole, phenetole, butyl phenyl ether, methoxytoluene, tetrahydrofuran, dibenzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol, methyl acetoacetate, ethyl acetoacetate, dimethyl maleate, dimethyl malonate, dimethyl succinate, dimethyl glutarate, dimethyl adipate, dimethyl phthalate, methyl cinnamate, ethyl cinnamate, toluene, xylene, tetralin, limonene, and an aliphatic hydrocarbon having a boiling point of from 30° to 300° C. which is selected from the group consisting of a straight-chain paraffin, an isoparaffin and a cycloparaffin.

Solvents which are particularly useful to provide a flux remover include water, methyl isobutyl carbinol, hexanol, heptanol, octanol, nonanol, 3-methylbutanol, propylene glycol, 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, tripropylene glycol monomethyl ether, tripropylene glycol monopropyl ether, tripropylene glycol monobutyl ether, propylene glycol dimethyl ether, dipropylene glycol dimethyl ether, tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone, methyl isoamyl ketone, acetophenone, propiophenone benzophenone, cyclohexanone, isophorone, pyrrolidone, N-methylpyrrolidone, dimethylformamide, dimethylacetamide, dimethyl sulfoxide sulfolane, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, methyl propionate, ethyl propionate, butyl propionate, benzyl propionate, methyl benzoate, ethyl benzoate, propyl benzoate, diethyl ether, dipropyl ether, dibutyl ether diphenyl ether, benzyl methyl ether, benzyl ethyl ether, anisole, methoxytoluene, tetrahydrofuran, dibenzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol, methyl acetoacetate, ethyl acetoacetate, dimethyl maleate, dimethyl malonate, dimethyl succinate, dimethyl glutarate, dimethyl adipate, dimethyl phthalate, toluene, xylene, tetralin, decalin, limonene, and an aliphatic hydrocarbon having a boiling point of from 30° to 300° C. which is selected from the group consisting of a straight-chain paraffin, an isoparaffin and a cycloparaffin.

Solvents which are particularly useful to provide a liquid crystal cell cleaner include water, heptanol, octanol, nonanol, 3-methylbutanol, propylene glycol, 3-methoxybutanol, 3-methyl-3-methoxybutanol, propylene glycol monomethyl ether propylene glycol monopropyl ether, propylene glycol monobutyl ether, dipropylene glycol monomethyl ether, dipropylene glycol monopropyl ether, dipropylene glycol monobutyl ether, tripropylene glycol monomethyl ether, tripropylene glycol monopropyl ether, propylene glycol dimethyl ether, dipropylene glycol dimethyl ether, tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone, methyl isoamyl ketone, acetophenone, propiophenone, benzophenone, cyclohexanone, pyrrolidone, N-methylpyrrolidone, dimethylformamide, dimethylacetamide, dimethyl sulfoxide, sulfolane, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, methyl propionate, ethyl propionate, butyl propionate, benzyl propionate, methyl benzoate, ethyl benzoate, propyl benzoate, diethyl ether, dipropyl ether, dibutyl ether, diphenyl ether, benzyl methyl ether, benzyl ethyl ether, anisole, phenetole, butyl phenyl ether, methoxytoluene, tetrahydrofuran, dibenzyl ether, acetonitrile, γ-butyrolactone, propylene carbonate, propylene glycol monomethyl ether acetate, propylene glycol monomethyl ether propionate, dipropylene glycol monoethyl ether acetate, propylene glycol diacetate, diacetone alcohol, methyl acetoacetate, ethyl acetoacetate, dimethyl maleate, dimethyl malonate, dimethyl succinate, dimethyl glutarate, dimethyl adipate, dimethyl phthalate, methyl cinnamate, ethyl cinnamate, toluene, xylene, tetralin, decalin, limonene, and an aliphatic hydrocarbon having a boiling point of from 30° to 300° C. which is selected from the group consisting of a straight-chain paraffin, an isoparaffin and a cycloparaffin.

Solvents which are particularly useful to provide a resist stripper include water, methyl isobutyl carbinol, heptanol, octanol, 3-methylbutanol, propylene glycol, 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, tripropylene glycol monomethyl ether, tripropylene glycol monopropyl ether, tripropylene glycol monobutyl ether, propylene glycol dimethyl ether, dipropylene glycol dimethyl ether, tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone, methyl isoamyl ketone, acetophenone, propiophenone, benzophenone, cyclohexanone, pyrrolidone, N-methylpyrrolidone, dimethyl-formamide, dimethylacetamide, dimethyl sulfoxide, sulfolane, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxy-propionate, ethyl 3-ethoxypropionate, 2-ethylhexyl acetate, cyclohexyl acetate, benzyl acetate, methyl propionate, ethyl propionate, butyl propionate, benzyl propionate, methyl benzoate, ethyl benzoate, propyl benzoate, isoamyl benzoate, benzyl benzoate, diethyl ether, dipropyl ether, dibutyl ether, diphenyl ether, benzyl methyl ether, benzyl ethyl ether, anisole, phenetole, butyl phenyl ether, methoxytoluene, tetrahydrofuran, dibenzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol, methyl acetoacetate, ethyl acetoacetate, dimethyl maleate, dimethyl malonate, dimethyl succinate, dimethyl glutarate, dimethyl adipate, dimethyl phthalate, toluene, xylene, tetralin limonene, and an aliphatic hydrocarbon having a boiling point of from 30° to 300° C. which is selected from the group consisting of a straight-chain paraffin, an isoparaffin and a cycloparaffin.

These organic solvents and water may be used either individually or in combination of two or more thereof. A combined use of the organic solvent or water makes it possible to appropriately improve or modify the cleaning properties, safety, ease in hand ling, and the like of the solvent composition of the present invention.

Alkyl oxyisobutyrates sometimes give rise to such problems as corrosion of their storage container or denaturation of themselves during storage or on use as a solvent or a cleaning agent, depending on the acid content thereof. The acid content of alkyl oxyisobutyrates is ascribed to hydrolysis products of alkyl oxyisobutyrates or unreacted material, and acidic substances used for the preparation of alkyl oxyisobutyrates. Such acidic substances include methacrylic acid, sulfuric acid, and acetic acid. If the acid content of the ester exceeds 0.5% by weight, the ester often corrodes a storage container made of carbon steel, or tinplate, or the ester itself undergoes denaturation. These phenomena also occur when an alkyl oxyisobutyrate is combined with other organic solvents for use as a solvent or a cleaning agent. However, such unfavorable phenomena are not observed with alkyl oxyisobutyrates whose acid content is not more than 0.5% by weight. Accordingly, in order to prevent corrosion of containers and denaturation of the esters themselves and provide stabile storage stability of the esters, it is preferable to use those esters having an acid content of not more than 0.5% by weight, still preferably not more than 0.4% by weight. It is practically difficult to completely remove the acid content, and a practical lower limit of the acid content of the alkyl oxyisobutyrates is about 0.0001% by weight, which level is not at all problematical for use in the present invention.

There are various methods available for adjusting the acid content of an alkyl oxyisobutyrate. For example, the acid content can be separated by precise distillation. Whatever method is followed, it is important to reduce the acid content to 0.5% by weight or less.

Since the alkyl oxyisobutyrates of the present invention have a high boiling point and a relatively low rate of evaporation, they are useful as high-boiling solvents. When compounded into mixed solvent systems, they bring about improvements in performance properties and workability of coating compositions, adhesives, ink compositions, etc., such as spreadability and smoothness of a coating film and effects on fusion of resins.

The content of the alkyl oxyisobutyrate in the solvent composition is usually not less than about 5% by weight and preferably not less than 10% by weight, depending on the use.

When used as a cleaning agent, the cleansing action of the solvent composition may be, improved, if desired, by using a surface active agent, such as a nonionic surface active agent (e.g., polyalkyleneoxides and alkanolamides), a anionic surface active agent (e.g., alkyl(aryl)sulfonic acids and alkylphosphonic acids) or a cationic surface active agent (e.g., long chain amines and quaternary ammonium salts), an acidic compound, or a basic compound in combination. The typical example of the surface active agent includes polyoxyethylene dodecyl ether, sodium dodecylbenzenesulfonic acid and trimethylbenzylammonium chloride. The typical example of the acidic compound includes acetic acid, α-methoxyisobutyric acid, β-methoxyisobutyric acid, α-hydroxyisobutyric acid and methacrylic acid. The typical example of the basic compound includes triethylamine and triethanolamine. The surface active agent, acidic compound and basic compound is preferably used in an amount of from about 0.01 to 30% by weight, more preferably from 0.1 to 10% by weight, based on the total solvent composition.

When used as a resist stripper, the solvent composition may further contain a stripping accelerator, such as benzenesulfonic acid, toluenesulfonic acid, xylenesulfonic acid, phenolsulfonic acid, and alkylbenzenesulfonic acids, e.g., methyl-, propyl-, heptyl-, octyl-, decyl- or dodecylbenzenesulfonic acid. The stripping accelerator is usually used in an amount of from about 5 to 30% by weight, preferably 7 to 20% by weight, based on the total solvent composition. To improve stripping properties, the composition may furthermore contain a surface active agent, such as a nonionic surface active agent, anionic surface active agent or a cationic surface active agent, an acidic compound, or a basic compound.

The oxyisobutyric esters of the present invention have very high dissolving power for various organic compounds, including high polymers and naturally-occurring compounds. On the other hand, the alkyl oxyisobutyrates of the present invention do not have risk of explosion at an ordinal temperature, because their ignition point is 40° C. or more. In addition, the acute toxicity (median lethal dose ($LD_{50}$); rat, oral) of the alkyl oxyisobutyrates is 2000 mg/kg or more. Therefore, they are also useful as an assistant for diluting solvents for agricultural chemicals or as a solvent or an assistant for cosmetics.

The photoresists to which the resist stripper of the present invention is applicable are not limited at all. That is, the resist stripper of the invention is useful for removal of any of positive or negative resists for optical alignment, resists for far ultraviolet light alignment, and resists for X-ray or electron beam alignment. Main materials known for these resists include novolak resins, cyclized rubbers, polysilicic acid, (meth)acrylic resins, (meth)acrylic acid copolymers, and polyhydroxystyrene. The resist stripper of the present invention is effective on any of these high polymers.

The present invention will now be illustrated in greater detail with reference to the Examples in view of the Comparative Examples, but the present invention should not be construed as being limited thereto. All of the mixing ratios of the solvents are given by weight unless otherwise indicated.

EXAMPLE 1

The compatibility of the alkyl oxyisobutyrates of the present invention with other solvents was examined as follows.

Methyl α-methoxyisobutyrate, methyl β-methoxyisobutyrate, methyl α-hydroxyisobutyrate or a 30/70 mixture of methyl β-methoxyisobutyrate and methyl α-hydroxyisobutyrate, and the solvents shown in Table 1 below were mixed in a mixing ratio of 1/1 by volume in an Erlenmeyer flask, and the mixture was allowed to stand still at room temperature. The degree Of compatibility was visually observed and rated as follows. The results obtained are shown in Table 1.

A . . . Completely uniformly mixed.
B . . . White turbidity observed.
C . . . Separated into two phases.

COMPARATIVE EXAMPLE 1

The compatibility of Cellosolve acetate (ethylene glycol monoethyl ether acetate; hereinafter abbreviated as "ECA") with the solvent shown in Table 1 was examined in the same manner as in Example 1. The results obtained are shown in Table 1 below.

TABLE 1

| Solvent | Example 1 | | | | Compar. Example 1 |
| --- | --- | --- | --- | --- | --- |
| | α-MBM[1] | β-MBM[2] | α-HBM[3] | β-MBM/ α-HBM[4] | ECA |
| Water | C | C | A | B | C |
| Methanol | A | A | A | A | A |
| Ethanol | A | A | A | A | A |
| Isopropyl alcohol | A | A | A | A | A |
| Ethyl acetate | A | A | A | A | A |
| Acetone | A | A | A | A | A |
| dimethylformamide | A | A | A | A | A |
| Acetonitrile | A | A | A | A | A |
| Benzene | A | A | A | A | A |
| Toluene | A | A | A | A | A |
| Xylene | A | A | A | A | A |
| n-Hexane | A | A | A | A | A |
| Cyclohexane | A | A | A | A | A |
| Cyclohexanone | A | A | A | A | A |
| Cyclohexanol | A | A | A | A | A |

Note:
[1] Methyl α-methoxyisobutyrate
[2] Methyl β-methoxyisobutyrate
[3] Methyl α-hydroxyisobutyrate
[4] β-MBM/α-HBM = 30/70

EXAMPLE 2

The rate of evaporation Of the alkyl oxyisobutyrates of the present invention was measured as follows.

The solvents shown in Table 2 below weighing 0.75 g, were uniformly spread on a disc of No. 4 filter paper having a diameter of 95 mm. The coated filter paper was allowed to stand on a testing stand at 25° C. with a covering over it. The sample was weighed at given time intervals to determine the evaporation loss, from which the rate of evaporation was calculated. The results obtained, expressed relatively taking the rate of evaporation of butyl acetate as a standard (100), are shown in Table 2 below.

TABLE 2

| Solvent | Relative Rate of Evaporation |
|---|---|
| Butyl acetate | 100 (standard) |
| Methyl α-hydroxyisobutyrate | 56 |
| Ethyl α-Hydroxyisobutyrate | 26 |
| Methyl α-methoxyisobutyrate | 64 |
| Methyl β-methoxyisobutyrate | 44 |
| Ethyl β-ethoxyisobutyrate | 16 |

COMPARATIVE EXAMPLE 2

The rate of evaporation of the conventional solvents shown in Table 3 below was determined in the same manner as in Example 2. The results obtained are shown in Table 3 below.

TABLE 3

| Solvent | Relative Rate of Evaporation |
|---|---|
| Butyl acetate | 100 (standard) |
| ECA | 22 |
| Ethyl lactate | 23 |
| Methyl β-methoxypropionate | 35 |

EXAMPLE 3

The dissolving power of methyl β-methoxyisobutyrate for various resins was evaluated as follows.

In a 100 ml-volume Erlenmeyer flask was put 2.0 g of the resins shown in Table 4 below, and 20 ml of methyl β-methoxyisobutyrate was added thereto. The mixture was kept at 25° C. while stirring, and the time required for the resin to dissolve was measured. The results obtained are shown in Table 4 below.

COMPARATIVE EXAMPLE 3

The dissolving power of ECA was evaluated in the same manner as in Example 3. The results are shown in Table 4 below.

TABLE 4

| Resin | Time for Dissolution (min) Example 3 | Time for Dissolution (min) Compar. Example 3 |
|---|---|---|
| Polyester (ER-1002, a product of Mitsubishi Rayon Co., Ltd.) | 110 | 150 |
| Polystyrene (QPX2B, a product of Denki Kagaku Kogyo K.K. | 46 | 86 |
| Methyl methacrylate-styrene copolymer (MS-300, a product of Nippon Steel Chemical Co., Ltd.) | 82 | 125 |
| Acrylonitrile-styrene copolymer (AS-30, a product of Asahi Chemical Industry Co., Ltd.) | 95 | 145 |
| Acrylic resin (Acrydic A-405, a product of Dainippon Ink and Chemicals, Inc.) | 30 | 45 |
| Phenoxy resin (PKH-H, a product of Union Carbide Corp.) | 110 | 150 |
| Polysulfone (P1800NT11, a product of Amoco Co.) | 160 | 260 |

EXAMPLE 4

The dissolving power of the solvent compositions according to the present invention for various organic resins was evaluated.

In a 100 ml-volume Erlenmeyer flask was put 2.0 g of each of the following resins 1* to 4*, and 20 ml of each of tho solvent compositions shown in Table 5 below was added thereto. The mixture was kept at 25° C. while stirring, and the time required for the resin to dissolve was measured. The results obtained are shown in Table 5 below.

Resins:

1* . . . Epoxy resin (Epikote 1007 a product of Yuka Shell Epoxy Co., Ltd.)

2* . . . Polyester (ER-1002, a product of Mitsubishi Rayon Co., Ltd.)

3* . . . Polystyrene (QPX2B, a product of Denki Kagaku Kogyo K.K.)

4* . . . Acrylic resin (Acrydic A-405, a product of Dainippon Ink and Chemicals, Inc.)

TABLE 5

| Solvent or Solvent Composition | Time for Dissolution (min) 1* | 2* | 3* | 4* |
|---|---|---|---|---|
| Ethyl α-ethoxyisobutyrate | 24 | 112 | 45 | 30 |
| Methyl α-hydroxyisobutyrate | 38 | 140 | 70 | 40 |
| Methyl α-methoxyisobutyrate/methyl α-hydroxyisobutyrate (50:50) | 29 | 125 | 50 | 35 |
| Methyl β-methoxyisobutyrate/methyl isobutyl ketone (80:10) | 26 | 130 | 60 | 33 |
| Methyl β-methoxyisobutyrate/methyl β-methoxypropionate (5:95) | 31 | 135 | 70 | 45 |
| Methyl βmethoxyisobutyrate/butyl acetate/cyclohexanone (80:10:10) | 27 | 120 | 50 | 40 |
| Methyl α-methoxyisobutyrate/2-ethyl-1-hexanol/dibenzyl ether (60:30:10) | 29 | 135 | 55 | 35 |
| Butyl α-butoxyisobutyrate/dipropylene glycol monomethyl ether acetate/ethyl acetoacetate (40:10:50) | 30 | 130 | 65 | 40 |
| Methyl α-methoxyisobutyrate/dimethylfomamide/3-methoxybutanol (5:50:45) | 30 | 140 | 70 | 40 |
| Ethyl β-ethoxyisobutyrate/N-methylpyrrolidone/tetralin (60:10:30) | 31 | 135 | 60 | 35 |
| Ethyl β-ethoxyisobutyrate/dimethyl adipate/γ-butyrolactone (30:30:40) | 24 | 115 | 55 | 31 |
| Ethyl α-ethoxyisobutyrate/acetophenone/naphthenic petroleum fraction (boiling point: 158–180° C.) (50:25:25) | 30 | 125 | 60 | 40 |
| Methyl α-hydroxyisobutyrate/tetrahydrofuran/dipropylene | 25 | 120 | 45 | 32 |

TABLE 5-continued

| Solvent or Solvent Composition | Time for Dissolution (min) | | | |
|---|---|---|---|---|
| | 1* | 2* | 3* | 4* |
| glycol dimethyl ether (60:20:20) | | | | |
| Methyl α-methoxyisobutyrate/ cyclohexanol/ethyl lactate (50:20:20) | 32 | 140 | 65 | 38 |
| Methyl α-methoxyisobutyrate/ propylene carbonate/methyl cinnamate (50:30:20) | 29 | 135 | 70 | 35 |

COMPARATIVE EXAMPLE 4

The dissolving power of ECA, ethyl lactate or methyl β-methoxypropionate for various resins was evaluated in the same manner as in Example 4. The results are shown in Table 6 below.

TABLE 6

| Solvent or Solvent Composition | Time for Dissolution (min) | | | |
|---|---|---|---|---|
| | 1* | 2* | 3* | 4* |
| ECA | 45 | 150 | 86 | 45 |
| Ethyl lactate | 65 | >300 | 145 | 105 |
| Methyl β-methoxypropionate | 42 | 195 | 105 | 70 |

TABLE 7

| Degreasing Agent | Degreasing Power | | |
|---|---|---|---|
| | Cutting Oil | Press Oil | Grease |
| Methyl α-methoxyisobutyrate | A | A | A |
| Methyl β-methoxyisobutyrate | A | A | A |
| Methyl β-methoxyisobutyrate/methyl α-hydroxyisobutyrate (30:70) | A | A | A |
| Ethyl β-ethoxyisobutyrate/ methyl isobutyl ketone (80:20) | A | A | A |
| Methyl β-ethoxyisobutyrate/ dimethylformamide (50:50) | A | A | A |
| Methyl β-methoxyisobutyrate/N-methylpyrrolidone/water (50:40:10) | A | A | A |
| Methyl α-methoxyisobutyrate/methyl β-methoxyisobutyrate (30:70) | A | A | A |
| Methyl α-hydroxyisobutyrate | A | A | B |
| Ethyl α-hydroxyisobutyrate/ethyl lactate/polyoxyethylene dodecyl ether (10:80:10) | A | A | A |
| Methyl β-methoxyisobutyrate/butyl acetate/octanol (50:20:30) | A | A | A |
| Methyl β-methoxyisobutyrate/ isophorone (70:30) | A | A | A |
| Methyl α-hydroxyisobutyrate/3-methoxybutyl acetate (50:50) | A | A | A |
| Methyl β-methoxyisobutyrate/amyl acetate/3-methoxybutanol (30:50:20) | A | A | A |
| Methyl α-hydroxyisobutyrate/N-methylpyrrolidone/water (30:50:20) | A | B | A |
| Methyl β-methoxyisobutyrate/2-ethylhexanol/dibenzyl ether (50:30:20) | A | A | A |
| Methyl β-methoxyisobutyrate/2-ethylhexyl acetate/benzyl alcohol (50:30:20) | A | A | A |
| Methyl α-methoxyisobutyrate/3,5,5-trimethyl-1-hexanol/benzyl acetate (40:30:30) | A | A | A |
| Methyl α-hydroxyisobutyrate/ cyclohexanol/cyclohexyl acetate (60:20:20) | A | A | A |

TABLE 7-continued

| Degreasing Agent | Degreasing Power | | |
|---|---|---|---|
| | Cutting Oil | Press Oil | Grease |
| Methyl α-methoxyisobutyrate/hexane (20:80) | A | A | A |
| Methyl β-methoxyisobutyrate/dodecane (60:40) | A | A | A |
| Ethyl α-methoxyisbutyrate/isooctane (50:50) | A | A | A |
| Methyl β-methoxyisobutyrate/kerosine (JIS #1) (30:70) | A | A | A |
| Ethyl β-ethoxyisobutyrate/petroleum naphtha (heavy) (80:20) | A | A | A |
| Methyl β-ethoxyisobutyrate/dimethylformamide/decane (50:20:30) | A | A | A |
| Methyl β-methoxyisobutyrate/N-methylpyrrolidone/decane (40:30:30) | A | A | A |
| Methyl β-methoxyisobutyrate/ naphthenic petroleum fraction (boiling point: 158–180° C.) (40:60) | A | A | A |
| Ethyl (α-hydroxyisobutyrate/methyl β-methoxyisobutyrate/kerosine (JIS #2)/polyoxyethylene dodecyl ether (10:40:40:10) | A | A | A |
| Methyl β-methoxyisobutyrate/benzyl ether/ligroin (10:20:70) | A | A | A |
| Methyl β-methoxyisobutyrate/dioxane/ naphthenic petroleum fraction (boiling point: 206–230° C.) (30:30:40) | A | A | A |
| Methyl β-methoxyisobutyrate/cyclohexanone/isoparaffinic synthetic hydrocarbon fraction (boiling point: 165–204° C.) (50:10:40) | A | A | A |
| Methyl α-hydroxyisobutyrate/xylene/ naphthenic petroleum fraction (boiling point: 212–233° C.) (30:40:30) | A | A | A |
| Methyl α-methoxyisobutyrate/methoxytoluene (10:90) | A | A | A |
| Methyl β-methoxyisobutyrate/ acetophenone (60:40) | A | A | A |
| Ethyl α-methoxyisobutyrate/benzyl propionate (50:50) | A | A | A |
| Methyl β-methoxyisobutyrate/ethyl benzoate (30:70) | A | A | A |
| Ethyl β-ethoxyisobutyrate/butyl phenyl ether (80:20) | A | A | A |
| Methyl β-ethoxyisobutyrate/ acetophenone/anisole (20:40:40) | A | A | A |
| Methyl β-methoxyisobutyrate/ diethyl phthalate/anisole (40:30:30) | A | A | A |
| Methyl β-methoxyisobutyrate/dibenzyl ether/acetophenone (10:70:20) | A | A | A |
| Ethyl α-hydroxyisobutyrate/methyl β-methoxyisobutyrate/benzophenone/ polyoxyethylene dodecyl ether (20:30:40:10) | A | A | A |
| Methyl β-methoxyisobutyrate/propiophenone/ethyl lactate (10:20:70) | A | A | A |
| Methyl β-methoxyisobutyrate/ benzophenone/N-methylpyrrolidone (30:30:40) | A | A | A |
| Methyl β-methoxyisobutyrate/cyclohexanone/dioxane/acetophenone (50:10:20:20) | A | A | A |
| Methyl α-hydroxyisobutyrate/ xylene/anisole/propiophenone (30:30:20:20) | A | A | A |
| Methyl β-methoxyisobutyrate/ethyl lactate (5:95) | A | B | A |
| Methyl β-methoxyisobutyrate/dipropylene glycol monomethyl ether acetate/ethyl acetoacetate (70:20:10) | A | A | A |
| Methyl α-hydroxyisobutyrate/ propylene glycol monomethyl ether | A | A | A |

TABLE 7-continued

| Degreasing Agent | Degreasing Power | | |
|---|---|---|---|
| | Cutting Oil | Press Oil | Grease |
| acetate/dimethyl succinate (80:10:10) | | | |
| Ethyl α-ethoxyisobutyrate/N-methyl-pyrrolidone (10:90) | A | A | B |

COMPARATIVE EXAMPLE 5

The conventional degreasing agents shown in Table 8 below were tested in the same manner as in Example 5. The results obtained are shown in Table 8 below.

TABLE 8

| Degreasing Agent | Degreasing Power | | |
|---|---|---|---|
| | Cutting Oil | Press Oil | Grease |
| 1,1,1-Trichloroethane | A | B | A |
| Freon 113 | A | C | B |
| Ethyl lactate | C | C | C |
| N-Methylpyrrolidone | B | C | C |

EXAMPLE 6

Various commercially available inks were uniformly spread on a 50 mm long, 20 mm wide, and 2 mm thick aluminum plate with a polished surface by means of a bar coder. One hour later, the coated aluminum plate was put in a washing bottle containing the ink removers shown in Table 9 below, and the bottle and content was shaken at room temperature for 30 seconds. The plate was taken out and dried. The ink remaining on the plate was observed with the naked eye and under a metallurgical microscope, and the ink removing power was evaluated according to the following rating system.

A . . . No residual ink was observed with the naked eye or under a metallurgical microscope.

B . . . Residual ink was not observed with the naked eye, but observed under a metallurgical microscope.

C . . . Residual ink was observed with the naked eye.

The results obtained are Shown in Table 9 below.

TABLE 9

| Ink Remover | Ink Removing Power | | | |
|---|---|---|---|---|
| | 1* | 2* | 3* | 4* |
| Methyl α-methoxyisobutyrate | A | A | A | A |
| Methyl β-methoxyisobutyrate | A | A | A | A |
| Methyl β-methoxyisobutyrate/methyl α-hydroxyisobutyrate (30:70) | A | A | A | B |
| Ethyl β-ethoxyisobutyrate/methyl isobutyl ketone (80:20) | A | A | A | A |
| Methyl β-ethoxyisobutyrate/dimethylformamide (50:50) | A | A | A | A |
| Methyl β-methoxyisobutyrate/N-methylpyrrolidone/water (50:40:10) | A | A | A | A |
| Methyl α-methoxyisobutyrate/methyl β-methoxyisobutyrate (30:70) | A | A | A | A |
| Methyl α-hydroxyisobutyrate | A | A | B | B |
| Ethyl α-hydroxyisobutyrate/ethyl lactate/dodecylbenzenesulfonic acid (10:80:10) | A | A | A | A |
| Methyl β-methoxyisobutyrate/butyl acetate/octanol (50:20:30) | A | A | A | A |
| Methyl β-methoxyisobutyrate/isophorone (70:30) | A | A | A | A |
| Methyl α-hydroxyisobutyrate/3-methoxybutyl acetate (50:50) | A | A | A | B |
| Methyl β-methoxyisobutyrate/amyl acetate/3-methoxybutanol (30:50:20) | A | A | A | A |
| Methyl α-hydroxyisobutyrate/N-methylpyrrolidone/water/acetic acid (30:50:15:5) | A | A | A | A |
| Methyl β-methoxyisobutyrate/2-ethylhexanol/dibenzyl ether (50:30:20) | A | A | A | A |
| Methyl β-methoxyisobutyrate/2-ethylhexyl acetate/benzyl alcohol (50:30:20) | A | A | A | A |
| Methyl α-methoxyisobutyrate/3,5,5-trimethyl-1-hexanol/benzyl acetate (40:30:30) | A | A | A | A |
| Methyl α-hydroxyisobutyrate/cyclohexanol/cyclohexyl acetate (60:20:20) | A | A | A | A |
| Methyl α-methoxyisobutyrate/octane (50:50) | A | A | A | A |
| Methyl β-methoxyisobutyrate/decane (90:10) | A | A | A | A |
| Ethyl α-methoxyisobutyrate/isooctane (20:80) | A | A | A | A |
| Methyl β-methoxyisobutyrate/1-octane (70:30) | A | A | A | A |
| Ethyl β-ethoxyisobutyrate/cyclohexane (60:40) | A | A | A | A |
| Methyl β-ethoxyisobutyrate/decalin (50:50) | A | A | A | A |
| Methyl β-methoxyisobutyrate/kerosine (JIS #1) (50:50) | A | A | A | A |
| Methyl α-methoxyisobutyrate/ligroin (30:70) | A | A | A | A |
| Methyl α-hydroxyisobutyrate/industrial gasoline (JIS #5) (60:40) | A | A | A | A |
| Ethyl α-hydroxyisobutyrate/methyl β-methoxyisobutyrate/kerosine (JIS #2) (20:40:40) | A | A | A | A |
| Methyl β-methoxyisobutyrate/butyl acetate/kerosine (JIS #2) (50:20:30) | A | A | A | A |
| Methyl β-methoxyisobutyrate/tetralin/ligroin (20:30:50) | A | A | A | A |
| Methyl β-methoxyisobutyrate/acetophenone/ligroin (30:40:30) | A | A | A | A |
| Methyl β-methoxyisobutyrate/naphthenic petroleum fraction (boiling point: 163–212° C.) (50:50) | A | A | A | A |
| Methyl α-hydroxyisobutyrate/isoparaffinic synthetic hydrocarbon fraction (boiling point: 165–204° C.) (30:70) | A | A | A | A |
| Methyl α-methoxyisobutyrate/acetophenone (50:50) | A | A | A | A |
| Methyl β-methoxyisobutyrate/benzyl methyl ether (80:20) | A | A | A | A |
| Ethyl -α-methoxyisobutyrate/anisole (40:60) | A | A | A | A |
| Methyl β-methoxyisobutyrate/benzophenone/benzyl acetate (60:20:20) | A | A | A | A |
| Ethyl β-ethoxyisobutyrate/diethyl phthalate (60:40) | A | A | A | A |
| Methyl β-ethoxyisobutyrate/methyl benzoate (50:50) | A | A | A | A |
| Methyl β-methoxyisobutyrate/methyl | A | A | A | A |

TABLE 9-continued

| Ink Remover | Ink Removing Power | | | |
|---|---|---|---|---|
| | 1* | 2* | 3* | 4* |
| cinnamate/ligroin (40:30:30) | | | | |
| Methyl β-methoxypropionate/propiophenone (30:70) | A | A | A | A |
| Ethyl β-ethoxypropionate/dioctyl phthalate (60:40) | A | A | A | A |
| Ethyl α-hydroxyisobutyrate/methyl β-methoxyisobutyrate/acetophenone (20:40:40) | A | A | A | A |
| Methyl β-methoxyisobutyrate/butyl acetate/acetophenone (50:20:30) | A | A | A | A |
| Methyl β-methoxyisobutyrate/anisole/acetophenone (30:20:50) | A | A | A | A |
| Methyl β-methoxyisobutyrate/acetophenone/ethyl lactate (20:20:60) | A | A | A | A |
| Methyl β-methoxyisobutyrate/benzophenone/dibenzyl ether (30:20:50) | A | A | A | A |
| Methyl β-methoxypropionate/acetophenone/benzyl ethyl ether (60:20:20) | A | A | A | A |
| Methyl β-methoxyisobutyrate/dipropylene glycol monomethyl ether (5:95) | A | A | A | A |
| Methyl β-methoxyisobutyrate/propylene glycol monomethyl ether (20:80) | A | A | A | A |
| Methyl α-hydroxyisobutyrate/propylene glycol mono-n-propyl ether (40:60) | A | B | A | B |
| Methyl β-methoxyisobutyrate/dipropylene glycol monomethyl ether/water (5:85:10) | A | A | A | A |
| Methyl β-methoxyisobutyrate/dipropylene glycol monomethyl ether/water (10:80:10) | A | A | A | A |
| Methyl β-ethoxyisobutyrate/propylene glycol mono-n-butyl ether (40:60) | A | B | A | A |
| Methyl α-hydroxyisobutyrate/dipropylene glycol mono-n-butyl ether (30:70) | A | B | A | B |
| Methyl β-methoxyisobutyrate/dipropylene glycol monomethyl ether/iospropanol (10:80:10) | A | A | A | A |
| Methyl α-hydroxyisobutyrate/dipropylene glycol monomethyl ether (10:90) | A | A | A | A |
| Methyl α-methoxyisobutyrate/propylene glycol mono-n-butyl ether (40:60) | A | A | A | A |
| Methyl β-methoxyisobutyrate/dipropylene alycol monomethyl ether/propylene glycol monomethyl ether (20:70:10) | A | A | A | A |
| Methyl β-methoxyisobutyrate/dipropylene glycol monomethyl ether/water (70:20:10) | A | A | A | A |
| Methyl α-hydroxyisobutyrate/dipropylene glycol monomethyl ether/propylene glycol monomethyl ether (10:80:10) | A | B | A | A |
| Methyl β-methoxyisobutyrate/ethyl acetoacetate/water (70:20:10) | A | A | A | A |
| Methyl β-methoxyisobutyrate/dipropylene glycol dimethyl ether/tetrahydrofuran (60:10:30) | A | A | A | A |
| Ethyl α-ethoxyisobutyrate/methyl β-methoxypropionate (5:95) | A | A | A | A |

Note:
1*: Cellulose resin-based green ink for printing letters on instrument boards
2*: Hot-setting green solder resist ink
3*: UV-curing white marking ink
4*: Vinyl chloride-acrylate copolymer-based white screen printing ink

COMPARATIVE EXAMPLE 6

The conventional ink removers shown in Table 10 below were tested in the same manner as in Example 6. The results obtained are shown in Table 10 below.

TABLE 10

| Ink Remover | Ink Removing Power | | | |
|---|---|---|---|---|
| | 1* | 2* | 3* | 4* |
| 1,1,1-Trichloroethane | A | B | A | C |
| Ethyl lactate | A | C | B | C |
| 1,1,1-Trichloroethane/cyclohexanone (80:20) | A | A | A | B |
| Methyl β-methoxypropionate | B | B | A | B |

EXAMPLE 7

A commercially available flux (Solderite flux B-111R, a product of Tamura Corporation) was uniformly applied to the entire surface of a base of a printed circuit board (a copper-clad laminate), preliminarily dried at 100° C. and baked at 220° C.

The coated base was cleaned by immersing in the flux removers shown in Table 11 below while shaking at room temperature for 5 minutes. The base was taken out, washed with water, and dried. The residual flux on the base was observed with the naked eye and under a metallurgical microscope, and rated as follows.

A ... No residual flux was observed with the naked eye or under a metallurgical microscope.

B ... Residual flux was not observed with the naked eye, but observed under a metallurgical microscope.

C ... Residual flux was observed with the naked eye.

The results obtained are shown in Table 11 below.

TABLE 11

| Flux Remover | Flux Removing Power |
|---|---|
| Methyl α-methoxyisobutyrate | A |
| Methyl β-methoxyisobutyrate | A |
| Methyl β-methoxyisobutyrate/methyl α-hydroxyisobutyrate (30:70) | A |
| Ethyl β-ethoxyisobutyrate/acetone (50:50) | A |
| Methyl β-ethoxyisobutyrate/dimethylformamide (50:50) | A |
| Methyl β-methoxyisobutyrate/N-Methyl-pyrrolidone/water (40:50:10) | A |
| Methyl α-methoxyisobutyrate/methyl β-methoxyisobutyrate (30:70) | A |
| Methyl α-methoxyisobutyrate/methyl α-hydroxyisobutyrate (7:93) | A |
| Methyl β-methoxyisobutyrate/methyl lactate (30:70) | A |
| Methyl β-methoxyisobutyrate/butyl acetate/octanol (50:20:30) | A |
| Methyl β-methoxyisobutyrate/isophorone (70:30) | A |
| Methyl α-methoxyisobutyrate/3-methoxybutyl acetate (50:50) | A |
| Methyl β-methoxyisobutyrate/amyl acetate/3-methoxybutanol (30:50:20) | A |
| Methyl β-methoxyisobutyrate/2-ethylhexanol/dibenzyl alcohol (50:30:20) | A |
| Methyl β-methoxyisobutyrate/2-ethylhexyl acetate/benzyl alcohol (50:30:20) | A |
| Methyl α-methoxyisobutyrate/3,5,5- | A |

TABLE 11-continued

| Flux Remover | Flux Removing Power |
|---|---|
| trimethyl-1-hexanol/benzyl acetate (40:30:30) | |
| Methyl α-hydroxyisobutyrate/cyclohexanol/cyclohexyl acetate (60:20:20) | A |
| Methyl β-methoxyisobutyrate/butyl acetate/tetralin (30:40:30) | A |
| Ethyl α-ethoxyisobutyrate/acetophenone/isoparaffinic synthetic hydrocarbon fraction (boiling point: 150–200° C.) (60:20:20) | A |
| Methyl β-methoxyisobutyrate/benzyl methyl ether (20:80) | A |
| Ethyl α-methoxyisobutyrate/anisole (70:30) | A |
| Methyl β-methoxyisobutyrate/benzophenone/benzyl acetate (10:40:50) | A |
| Ethyl β-ethoxyisobutyrate/diethyl phthalate (60:40) | A |
| Methyl β-ethoxyisobutyrate/methyl benzoate (5:95) | A |
| Methyl β-methoxyisobutyrate/methyl cinnamate/ligroin (40:30:30) | A |
| Methyl β-methoxypropionate/propiophenone (30:70) | A |
| Ethyl β-ethoxypropionate/dioctyl phthalate (60:40) | A |
| Methyl β-ethoxyisobutyrate/dimethylformamide/decane (20:20:60) | A |
| Methyl β-methoxyisobutyrate/N-methylpyrrolidone/decane (40:30:30) | A |
| Methyl β-methoxyisobutyrate/naphthenic petroleum fraction (boiling Point: 158–180° C.) (40:60) | A |
| Methyl α-methoxyisobutyrate/propylene glycol mono-n-butyl ether (40:60) | A |
| Methyl β-methoxyisobutyrate/dipropylene glycol monomethyl ether/propylene glycol monomethyl ether (20:70:10) | A |
| Methyl β-methoxyisobutyrate/dipropylene glycol monomethyl ether/water (70:20:10) | A |
| methyl α-hydroxyisobutyrate/dipropylene glycol monomethyl ether/propylene glycol monomethyl ether (10:80:10) | A |
| methyl β-methoxyisobutyrate/methyl acetoacetate/γ-butyrolactone (40:40:20) | A |
| Ethyl α-hydroxyisobutyrate/tetrahydrofuran/water (40:50:10) | A |

COMPARATIVE EXAMPLE 7

The conventional flux removers shown in Table 12 below were tested in the same manner as in Example 7. The results obtained are shown in Table 12 below.

TABLE 12

| Flux Remover | Flux Removing Power |
|---|---|
| Freon 113 | C |
| Methyl lactate | B |

EXAMPLE 8

A commercially available flux (Tamura F-A1-4, a product of Tamura Corporation) was uniformly applied to the entire surface of a base of a printed circuit board (a copper-clad laminate), preliminarily dried at 100° C., and baked at 220° C.

The coated base was cleaned by immersing in the flux removers shown in Table 13 below while shaking at 40° C. for 5 minutes. The base was taken out, washed with water, and dried. The residual flux on the base was observed with the naked eye and under a metallurgical microscope, and rated according to the same standard as in Example 7.

The results obtained are shown in Table 13 below.

TABLE 13

| Flux Remover | Flux Removing Power |
|---|---|
| Methyl α-hydroxyisobutyrate | A |
| Ethyl α-hydroxyisobutyrate | A |
| Methyl α-hydroxyisobutyrate/dimethylformamide (70:30) | A |
| Isopropyl α-hydroxyisobutyrate | A |
| Methyl α-hydroxyisobutyrate/water (90:10) | A |
| Methyl α-hydroxyisobutyrate/methyl lactate (50:50) | A |
| Methyl α-hydroxyisobutyrate/methyl β-methoxyisobutyrate (70:30) | A |
| Methyl α-hydroxyisobutyrate/butyl acetate/octanol (40:30:30) | A |
| Ethyl α-hydroxyisobutyrate/3-methyl-3-methoxybutanol/cyclohexanone (10:40:50) | A |
| Methyl α-hydroxyisobutyrate/2-ethylhexanol/dibenzyl ether (50:30:20) | A |
| Methyl α-hydroxyisobutyrate/2-ethylhexyl acetate/benzyl alcohol (50:30:20) | A |
| Methyl α-hydroxyisobutyrate/cyclohexanol/cyclohexyl acetate (60:20:20) | A |

COMPARATIVE EXAMPLE 8

The conventional flux removers shown in Table 14 below were tested in the same manner as in Example 8. The results obtained are shown in Table 14 below.

TABLE 14

| Flux Remover | Flux Removing Power |
|---|---|
| Freon 113 | C |
| Methyl lactate | B |

EXAMPLE 9

A liquid crystal cell assembled from a pair of glass plates (60×30×1 mm), with the surface having been cleaned, and spacers to have a cell gap of 10 μm was filled with a commercially available liquid crystal (ZLI-1565, a product of Merck Japan Co., Ltd.) and sealed.

The liquid crystal cell was washed by soaking in 100 ml of the cell cleaners shown in Table 15 below at room temperature for 10 minutes. The cell was taken out and dried in hot air. The liquid crystal remaining on the glass plates and the periphery of the cell was observed with the naked eye and a polarizing microscope, and rated as follows.

A . . . No residual liquid crystal was observed with the naked eye or under a polarizing microscope.

B . . . Residual liquid crystal was not observed with the naked eye, but observed under a polarizing microscope.

C . . . Residual liquid crystal was observed with the naked eye.

The results obtained are shown in Table 15 below.

TABLE 15

| Liquid Crystal Cleaner | Liquid Crystal Removing Power |
|---|---|
| Methyl α-methoxyisobutyrate | A |
| Methyl β-methoxyisobutyrate | A |
| Ethyl α-methoxyisobutyrate/isopropyl alcohol (50:50) | A |
| Methyl β-methoxyisobutyrate/methyl α-hydroxyisobutyrate (30:70) | A |
| Ethyl β-ethoxyisobutyrate/methyl isobutyl ketone (80:20) | A |
| Methyl β-methoxyisobutyrate/dimethylformamide (50:50) | A |
| Methyl β-methoxyisobutyrate/N-methylpyrrolidone (50:50) | A |
| Methyl α-methoxyisobutyrate/methyl β-methoxyisobutyrate (30:70) | A |
| Methyl α-hydroxyisobutyrate | B |
| Methyl β-methoxyisobutyrate/ethyl lactate/dodecylbenzenesulfonic acid (50:40:10) | A |
| Methyl β-methoxyisobutyrate/butyl acetate/octanol (50:20:30) | A |
| Methyl β-methoxyisobutyrate/isophorone (70:30) | A |
| Methyl α-hydroxyisobutyrate/3-methoxybutyl acetate (50:50) | A |
| Methyl β-methoxyisobutyrate/amyl acetate/3-methoxybutanol (30:50:20) | A |
| Methyl α-hydroxyisobutyrate/N-methylpyrrolidone/water/polyoxyethylene dodecyl ether (40:40:15:5) | A |
| Methyl β-methoxyisobutyrate/2-ethylhexanol/dibenzyl ether (50:30:20) | A |
| Methyl β-methoxyisobutyrate/2-ethylhexyl acetate/benzyl alcohol (50:30:20) | A |
| Methyl α-methoxyisobutyrate/3,5,5-trimethyl-1-hexanol/benzyl acetate (40:30:30) | A |
| Methyl α-hydroxyisobutyrate/cyclohexanol/cyclohexyl acetate (60:20:20) | A |
| Methyl α-methoxyisobutyrate/methoxytoluene (10:90) | A |
| Methyl β-methoxyisobutyrate/acetophenone (60:40) | A |
| Ethyl α-methoxyisobutyrate/ethyl acetoacetate (50:50) | A |
| Methyl β-methoxyisobutyrate/ethyl lactate (5:95) | A |
| Ethyl β-ethoxyisobutyrate/butyl phenyl ether (80:20) | A |
| Methyl β-ethoxyisobutyrate/acetophenone/anisole (50:30:20) | A |
| Methyl β-methoxyisobutyrate/diethyl phthalate/anisole (40:30:30) | A |
| Ethyl α-hydroxyisobutyrate/methyl methoxyisobutyrate/kerosene (JIS #2)/polyoxyethylene dodecyl ether (10:40:40:10) | A |
| Methyl β-methoxyisobutyrate/benzyl ether/ligroin (20:50:30) | A |
| Methyl β-methoxyisobutyrate/dioxane/naphthenic petroleum fraction (boiling point: 206–230° C.) (30:30:40) | A |
| Methyl α-hydroxyisobutyrate/propylene glycol mono-n-propyl ether (40:60) | A |
| Methyl β-methoxyisobutyrate/dipropylene glycol dimethyl ether/water (5:85:10) | A |
| Methyl β-methoxyisobutyrate/tripropylene glycol monomethyl ether/water (10:80:10) | A |

COMPARATIVE EXAMPLE 9

The conventional cell cleaners shown in Table 16 below were tested in the same manner as in Example 9. The results obtained are shown in Table 16 below.

TABLE 16

| Liquid Crystal Cleaner | Liquid Crystal Removing Power |
|---|---|
| 1,1,1-Trichloroethane | B |
| Polyoxyethylene butyl ether/ethanol/water (30:35:35) | C |
| Ethyl lactate | C |
| Methyl β-methoxypropionate | B |

EXAMPLE 10

A silicon wafer was uniformly coated with a commercially available positive photoresist for fine processing (OFPR-800, a product of Tokyo Ohka Kogyo Co., Ltd.) with a spinner (3000 rpm), pre-baked at 90° C. for minutes, and exposed to ultraviolet light to form a 30 pattern. The resist was developed with an alkali developer (NMD-W, a product of Tokyo Ohka Kogyo Co., Ltd.) at 25° C. for 1 minute, rinsed with pure water for 30 minutes, and post baked at 130° C. for 30 minutes. Then, the resist was removed by immersing in the resist strippers shown in Table 17 below for 5 minutes while shaking, washed with water, and dried. The residual resist film was observed with the naked eye and under a metallurgical microscope, and rated as follows.

A . . . No residual resist was observed with the naked eye or under a metallurgical microscope.

B . . . Residual resist was not observed with the naked eye, but observed under a metallurgical microscope.

C . . . Residual resist was observed with the naked eye. The results obtained are shown in Table 17 below.

TABLE 17

| Resist Stripper | Resist Removing Power |
|---|---|
| Methyl α-methoxyisobutyrate | A |
| Methyl β-methoxyisobutyrate | A |
| Methyl β-methoxyisobutyrate/methyl α-hydroxyisobutyrate/dodecylbenzenesulfonic acid (15:70:15) | A |
| Ethyl β-ethoxyisobutyrate/acetone (80:20) | A |
| Methyl β-ethoxyisobutyrate/dimethylformamide (50:50) | A |
| Methyl β-methoxyisobutyrate/N-methylpyrrolidone/water (50:40:10) | A |
| Methyl α-methoxyisobutyrate/methyl β-methoxyisobutyrate (30:70) | A |
| Methyl α-hydroxyisobutyrate | A |
| Ethyl α-hydroxyisobutyrate/ethyl lactate/dodecylbenzenesulfonic acid (10:70:20) | A |
| Ethyl α-hydroxyisobutyrate/methyl methoxyisobutyrate/benzophenone/polyoxyethylene dodecyl ether (20:30:40:10) | A |
| Methyl β-methoxyisobutyrate/propiophenone/ethyl lactate (10:20:70) | A |
| Methyl β-methoxyicobutyrate/benzophanone/N-methylpyrrolidone (30:30:40) | A |
| Methyl β-methoxyisobutyrate/butyl acetate/kerosine (JIS #2) (50:20:30) | A |
| Methyl β-methoxyisobutyrate/tetralin/ligroin (20:30:50) | A |

TABLE 17-continued

| Resist Stripper | Resist Removing Power |
|---|---|
| Ethyl α-methoxyisobutyrate/anisole (40:60) | A |
| Methyl β-methoxyisobutyrate/ethyl acetoacetate/tetrahydrofuran (60:20:20) | A |
| Ethyl β-ethoxyisobutyrate/γ-butyrolactone/ dipropylene glycol monomethyl ether (60:30:10) | A |
| Methyl α-hydroxyisobutyrate/propylene glycol monomethyl ether/water (20:70:10) | A |
| Methyl β-methoxyisobutyrate/methyl methoxypropionate (5:95) | A |

COMPARATIVE EXAMPLE 10

The conventional resist strippers shown in Table 18 below were tested in the same man: her as in Example 10. The results obtained are shown in Table 18 below.

TABLE 18

| Resist Stripper | Resist Removing Power |
|---|---|
| ECA | C |
| Ethyl lactate | C |
| Ethyl lactate/dodecylbenzene-sulfonic acid (80:20) | B |
| Methyl β-methoxypropionate | B |
| Methyl β-methoxypropionate/ dodecylbenzenesulfonic acid (80:20) | A |

EXAMPLE 11 AND COMPARATIVE EXAMPLE 11

Into a carbon steel (SS-41)-made drum having a diameter of 50 cm and a height of 80 cm was sealed 50 kg of methyl β-methoxyisobutyrate having various acid contents shown in Table 19 below. The drums were stored in a place shielded from direct sunlight at a storage temperature set at 15° to 30° C. for 1 year. The contents were taken out every 3 months to analyze the purity of the ester and to observe the outer appearance of the contents and the drum material. The results obtained are shown in Table 19 below.

TABLE 19

| Storage Time | Item of Analysis and Observation | Example 11 | | Comparative Example 11 | |
|---|---|---|---|---|---|
| Initial | Ester parity (wt %) | 99.6 | 99.3 | 99.1 | 99.0 |
| | Acid content (wt %): | | | | |
| | Sulfuric acid | 0.062 | — | 0.45 | — |
| | Acetic acid | — | 0.30 | — | 0.61 |
| | Methacrylic acid | 0.023 | 0.05 | 0.18 | 0.20 |
| | Total | 0.085 | 0.35 | 0.63 | 0.81 |
| | Appearance of ester | colorless and transparent | colorless and transparent | colorless and transparent | colorless and transparent |
| 3 Mts. | Ester parity (wt %) | 99.6 | 99.3 | 98.6 | 99.1 |
| | Appearance of ester | no change | no change | no change | pale yellow |
| | Appearance of drum | no change | no change | no change | black specks |
| 6 Mts. | Ester parity (wt %) | 99.6 | 99.2 | 97.5 | 96.8 |
| | Appearance of ester | no change | no change | no change | pale yellow |
| | Appearance of drum | no change | no change | no change | black specks |
| 9 Mts. | Ester parity (wt %) | 99.5 | 99.2 | 96.0 | 94.7 |
| | Appearance of ester | no change | no change | pale yellow | yellow |
| | Appearance of drum | no change | no change | black specks | almost all over blackened |
| 12 Mts. | Ester purity (wt %) | 99.5 | 99.1 | 94.1 | 92.0 |
| | Appearance of ester | no change | no change | yellow | dark yellow |
| | Appearance of drum | no change | no change | black specks | all over blackened |

EXAMPLE 12 AND COMPARATIVE EXAMPLE 12

Into a carbon steel (SS-41)-made drum having a diameter of 50 cm and a height of 80 cm was sealed 50 kg of methyl α-hydroxyisobutyrate having various acid contents shown in Table 20 below. The drums were stored in a place shielded from direct sunlight at a storage temperature set at 15° to 30° C. for 1 year. The contents were taken out every 3 months to analyze the purity of the ester and to observe the outer appearance of the contents and the drum material. The results obtained are shown in Table 20 below.

TABLE 20

| Storage Time | Item of Analysis and Observation | Example 12 | | Comparative Example 12 | |
|---|---|---|---|---|---|
| Initial | Ester parity (wt %) | 99.77 | 99.51 | 99.19 | 98.96 |
| | Acid content (wt %): | | | | |
| | Sulfuric acid | 0.05 | — | 0.45 | — |
| | α-Hydroxyisobutric acid | 0.02 | 0.06 | 0.18 | 0.72 |
| | Total | 0.07 | 0.06 | 0.63 | 0.72 |
| | Appearance of ester | colorless and transparent | colorless and transparent | colorless and transparent | colorless and transparent |
| 3 Mts. | Ester parity (wt %) | 99.71 | 99.37 | 98.74 | 98.49 |
| | Appearance of ester | no change | no change | no change | pale yellow |
| | Appearance of drum | no change | no change | no change | black specks |
| 6 Mts. | Ester parity (wt %) | 99.70 | 99.29 | 97.28 | 96.75 |
| | Appearance of ester | no change | no change | pale yellow | pale yellow |
| | Appearance of drum | no change | no change | no change | black specks |
| 9 Mts. | Ester parity (wt %) | 99.62 | 99.23 | 95.81 | 94.61 |
| | Appearance of ester | no change | no change | pale yellow | yellow |
| | Appearance of drum | no change | no change | black specks | almost all over blackened |
| 12 Mts. | Ester purity (wt %) | 99.46 | 99.15 | 93.27 | 92.08 |
| | Appearance of ester | no change | no change | yellow | dark yellow |
| | Appearance of drum | no change | no change | black specks | all over blackened |

EXAMPLE 13 AND COMPARATIVE EXAMPLE 13

Solvent compositions shown in Tables 21 and 22 below were prepared by using alkyl oxyisobutyrates having varied acid contents shown in the Tables and stored for 1 year under the same conditions as in Example 11. The contents were taken out of the drum every months, and the outer appearance of the contents and the drum material was observed. The results obtained are shown in Tables 21 and 22 below.

Solvent Composition:

1* . . . Methyl β-methoxyisobutyrate/2-ethyl-1-hexanol/dipropylene glycol monomethyl ether (60:20:20)

2* . . . Ethyl β-ethoxyisobutyrate isobutyl ketone/tetralin (70:10:20)

3* . . . Methyl α-hydroxyisobutyrate/acetophenone/propylene carbonate (80:10:10)

4* . . . Methyl α-methoxyisobutyrate/dimethylformamide/ethyl acetoacetate (80:10:10)

5* . . . Butyl β-butoxyisobutyrate/dibenzyl ether (70:30)

6* . . . Ethyl α-hydroxyisobutyrate/γ-butyrolactone/cyclohexane (70:20:10)

TABLE 21

| | Example 13 | | | Comparative Example 13 | | |
|---|---|---|---|---|---|---|
| Solvent Composition No. | 1* | 2* | 3* | 1* | 2* | 3* |
| Acid Content of Ester (wt %): | | | | | | |
| Sulfuric acid | 0.21 | — | 0.05 | 0.35 | — | 0.42 |
| Acetic acid | — | 0.09 | — | — | 0.40 | — |
| Methacrylic acid | 0.20 | 0.11 | — | 0.22 | 0.41 | — |
| α-Hydroxyisobutyric acid | — | — | 0.07 | — | — | 0.21 |
| Total | 0.41 | 0.20 | 0.12 | 0.57 | 0.81 | 0.63 |
| Initial Appearance of Solvent Composition | colorless and transparent | colorless and transparent | colorless and transparent | colorless and transparent | colorless and transparent | colorless and transparent |
| After 6 Mts. Storage: | | | | | | |
| Appearance of solvent composition | colorless and transparent | colorless and transparent | colorless and transparent | pale yellow | pale yellow | yellow |

TABLE 21-continued

|  | Example 13 | | | Comparative Example 13 | | |
|---|---|---|---|---|---|---|
| Solvent Composition No. | 1* | 2* | 3* | 1* | 2* | 3* |
| Appearance of drum | no change | no change | no change | black specks | black specks | black specks |
| After 12 Mts. Storage: | | | | | | |
| Appearance of solvent composition | colorless and transparent | colorless and transparent | colorless and transparent | yellow | yellow | brown |
| Appearance of drum | no change | no change | no change | black specks | black specks | all over blackened |

TABLE 22

|  | Example 13 | | | Comparative Example 13 | | |
|---|---|---|---|---|---|---|
| Solvent Composition No. | 4* | 5* | 6* | 7* | 8* | 9* |
| Acid content (wt %): | | | | | | |
| Sulfuric acid | 0.01 | — | 0.33 | 0.25 | — | 0.05 |
| Acetic acid | — | 0.08 | — | — | 0.18 | — |
| Methacrylic acid | — | 0.11 | — | 0.65 | 0.35 | — |
| α-Hydroxyisobutric acid | — | — | 0.07 | — | — | 0.65 |
| Total | 0.01 | 0.19 | 0.40 | 0.90 | 0.53 | 0.70 |
| Initial Appearance of Solvent Composition | colorless and transparent | colorless and transparent | colorless and transparent | colorless and transparent | colorless and transparent | colorless and transparent |
| After 6 Mts. Storage: | | | | | | |
| Appearance of solvent composition | colorless and transparent | colorless and transparent | colorless and transparent | yellow | colorless and transparent | pale yellow |
| Appearance of drum | no change | no change | no change | black specks | no change | black specks |
| After 12 Mts. Storage: | | | | | | |
| Appearance of solvent composition | colorless and transparent | colorless and transparent | colorless and transparent | yellow | pale yellow | yellow |
| Appearance of drum | no change | no change | no change | black specks | black specks | black specks |

As described above, the solvent composition according to the present invention has excellent dissolving power, gives off no offensive smell, gives rise to no environmental problem, and is safe. Additionally, the solvent composition of the present invention has the following advantages:

1) It has an extremely high dissolving power for natural and synthetic high polymers;
2) It is freely miscible with many organic solvents;
3) It is biodegradable, non-accumulating in nature;
4) It has low toxicity, no teratogenicity, and high safety;
5) It has a relatively high boiling point and ignition point, so as to secure improved handling properties and safety; and
6) It is non-corrosive for a substrate.

The degreasing agent comprising the solvent composition of the present invention has high cleaning power. Since the degreasing agent has an extremely high dissolving power for various fats and oils as well as the abovementioned advantages, it exhibits excellent ability in removal of fats, oils, and grease. Being water-soluble, the degreasing agent can be used in an aqueous system.

The ink remover comprising the solvent composition of the present invention has extremely high dissolving power for various types of inks, as well as the above-mentioned advantages, and therefore exhibits excellent ability in ink removal.

The flux remover comprising the solvent composition of the present invention exhibits an extremely high dissolving power for fluxes, as well as the above-mentioned advantages (1) to (6), and therefore has excellent ability in flux removal.

The liquid crystal cell cleaner comprising the solvent composition of the present invention has an extremely high dissolving power for various liquid crystals, as well as the above-mentioned advantages (1) to (6), and therefore exhibits excellent ability in removal of liquid crystals, and particularly contaminants from liquid crystal cells.

The resist stripper comprising the solvent composition of the present invention has an extremely high dissolving power for a photoresist, in addition to the abovementioned effects (1) to (6), and exhibits excellent performance in removal of a resist.

While the invention has been described in detail and with reference to specific examples thereof, it will be apparent to one skilled in the art that various changes and modifications can be made therein without departing from the spirit and scope thereof.

What is claimed is:

1. A method for dissolving a polymeric compound which comprises administering to the polymeric compound in need of such treatment an effective amount of a solvent composition comprising, as an active component, at least 5% by weight of at least one oxyisobutyric acid ester, wherein said oxyisobutyric acid ester is selected from the group consisting of an alkyl α-alkoxyisobutyrate represented by formula (I):

an alkyl β-alkoxyisobutyrate represented by formula (II):

and an alkyl α-hydroxyisobutyrate represented by formula (III):

wherein $R^1$ and $R^2$ each represent an alkyl group having from 1 to 4 carbon atoms.

2. A method as claimed in claim 1, wherein said polymeric compound is selected from the group consisting of epoxy resins, acrylic resins, vinyl resins, alkyd resins, polyester resins, novolak resins, polystyrene resins, phenoxy resins, polysulfone, methyl methacrylate.styrene copolymer, acrylonitrile.styrene copolymer and general hydrocarbon-based fats.

3. A method as claimed in claim 2, wherein said polymeric compound is selected from the group consisting of polyester resins, polystyrene resins, acrylic resins, epoxy resins, phenoxy resins, polysulfone, methyl methacrylate.styrene copolymer and acrylonitrile.styrene copolymer.

4. A method as claimed claim 1, wherein said composition further comprises at least one compound selected from the group consisting of water, methyl isobutyl carbinol, hexanol, heptanol, octanol, nonanol, 3-methylbutanol, propylene glycol; 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, tripropylene glycol monoethyl ether, tripropylene glycol monobutyl ether, tripropylene glycol monobutyl ether, propylene glycol dimethyl ether, dipropylane glycol dimethyl ether tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone, methyl isoamyl ketone, acetophenone, propiophenone, benzophenone, cyclohexanone, isophorone, pyrrolidone, N-methylpyrrolidone, dimethylformamide, dimethylacetamide, dimethyl sulfoxide, sulfolane, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, methyl propionate, ethyl propionate, butyl propionate, benzyl propionate, methyl benzoate, ethyl benzoate, propyl benzoate, isoamyl benzoate, benzyl benzoate, diethyl ether, dibutyl ether, dibutyl ether, diphenyl ether, benzyl methyl ether, benzyl ethyl ether, anisole, phenetole, butyl phenyl ether, methoxytoluene, tetrahydrofuran, dibenzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol methyl acetoacetate, ethyl acetoacetate, dimethyl maleate, malonate, dimethyl succinate, dimethyl succinate, dimethyl glutarate, dimethyl adipate, dimethyl phthalate, methyl cinnamate, ethyl cinnamate, toluene, xylene, tetralin, decalin, limonene, and an aliphatic hydrocarbon having a boiling point of from 30° to 300° C. which is selected from the group consisting of a straight-chain paraffin, an isoparaffin and a cycloparaffin.

5. The method as claimed in claim 1, wherein said oxyisobutyric acid ester is selected from the group consisting of methyl α-methoxyisobutyrate, ethyl α-methoxyisobutyrate, methyl α-ethoxyisobutyrate, ethyl α-ethoxyisobutyrate, methyl β-methoxyisobutyrate, ethyl β-methoxyisobutyrate, methyl β-ethoxyisobutyrate, ethyl β-ethoxyisobutyrate, methyl β-isopropoxyisobutyrate, ethyl β-isopropoxyisobutyrate, isopropyl β-isopropoxyisobutyrate, butyl β-isopropoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, isopropyl α-hydroxyisobutyrate, and butyl α-hydroxyisobutyrate.

6. The method as claimed in claim 1, wherein said oxyisobutyric acid ester has an acid content of from 0.0001 to 0.5% by weight.

7. A method for removing fats and oils on a surface which comprises administering to surface in need of such treatment an effective amount of a solvent composition comprising, as an active component, at least 10% by weight of at least one oxyisobutyric acid ester, wherein said oxyisobutyric acid ester as selected from the group consisting of an alkyl α-alkoxyisobutyrate represented by formula (I):

an alkyl β-alkoxyisobutyrate represented by formula (II):

and an alkyl α-hydroxyisobutyrate represented by formula (III):

wherein $R^1$ and $R^2$ each represent an alkyl group having from 1 to 4 carbon atoms.

8. A method as claimed in claim 7, wherein said composition further comprises at least one compound selected from the group consisting of water, hexanol, heptanol, octanol, 3-methylbutanol, propylene glycol, 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, tripropylene glycol monomethyl ether, tripropylene glycol monopropyl ether, propylene glycol dimethyl ether, dipropylene glycol dimethyl ether, tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone methyl isoamyl ketone, acetophenone, propiophenone, benzophenone, cyclohexanone isophorone, pyrrolidone, N-methylpyrrolidone, dimethylformamide, dimethylacetamide, dimethyl sulfoxide, sulfolane, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, methyl propionate, ethyl propionate, butyl propionate, benzyl propionate, methyl benzoate, ethyl benzoate, propyl benzoate, isoamyl benzoate, benzyl benzoate, diethyl ether, dipropyl ether, dibutyl ether, diphenyl ether, benzyl methyl ether, benzyl ethyl ether, anisole, phenetole, butyl phenyl ether, methoxytoluene, tetrahydrofuran, dibenzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol, methyl acetoacetate, ethyl acetoacetate, dimethyl maleate, dimethyl malonate, dimethyl succinate, dimethyl glutarate, dimethyl adipate, dimethyl phthalate, toluene, xylene, tetralin, decalin, limonene, and an aliphatic hydrocarbon having a boiling point of from 30° to 300° C. which is selected from the group consisting of a straight-chain paraffin, an isoparaffin and a cycloparaffin.

9. The method as claimed in claim 7, wherein said oxyisobutyric acid ester is selected from the group consisting of methyl α-methoxyisobutyrate, ethyl α-methoxyisobutyrate, methyl α-thoxyisobutyrate, ethyl α-ethoxyisobutyrate, methyl β-methoxyisobutyrate, ethyl β-methoxyisobutyrate, methyl β-ethoxyisobutyrate, ethyl β-ethoxyisobutyrate, methyl β-isopropoxyisobutyrate, ethyl β-isopropoxyisobutyrate, isopropyl β-isopropoxyisobutyrate, butyl β-isopropoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, isopropyl α-hydroxyisobutyrate, and butyl α-hydroxyisobutyrate.

10. The method as claimed in claim 7, wherein said oxyisobutyric acid ester has an acid content of from 0.0001 to 0.5% by weight.

11. A method for removing ink from a surface which comprises administering to a surface in need of such treatment an effective amount of a solvent composition comprising, as an active component, at least 5% by weight of at least one oxyisobutyric acid ester, wherein said oxyisobutyric acid ester is selected from the group consisting of an alkyl α-alkoxyisobutyrate represented by formula (I):

(I)

an alkyl β-alkoxyisobutyrate represented by formula (II):

(II)

and an alkyl α-hydroxyisobutyrate represented by formula (III):

(III)

wherein $R^1$ and $R^2$ each represent an alkyl group having from 1 to 4 carbon atoms.

12. A method as claimed in claim 11, wherein said composition further comprises at least one compound selected from the group consisting of water, methyl isobutyl carbinol, octanol, nonanol, 3-methylbutanol, propylene glycol, 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, tripropylene glycol monomethyl ether, tripropylene glycol monopropyl ether, tripropylene glycol monobutyl ether, propylene glycol dimethyl ether, dipropylene glycol dimethyl ether, tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone, methyl isoamyl ketone, acetophenone, propiophenone, benzophenone, cyclohexanone, isophorone, pyrrolidone, N-methylpyrrolidone, dimethylformamide, dimethylacetamide, dimethyl sulfoxide, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, methyl propionate, ethyl propionate, butyl propionate, benzyl propionate, methyl benzoate, ethyl benzoate, propyl benzoate, isoamyl benzoate, benzyl benzoate, diethyl ether, dipropyl ether, dibutyl ether, diphenyl ether, benzyl methyl ether, benzyl ethyl ester, anisole, phenetole, butyl phenyl ether, methoxytoluene, tetrahydrofuran, dibenzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol, methyl, acetoacetate, ethyl acetoacetate, dimethyl maleate, dimethyl malonate, dimethyl succinate, dimethyl glutarate, dimethyl adipate, dimethyl phthalate, methyl cinnamate, ethyl cinnamate, toluene, xylene, tetralin, limonene, and an aliphatic hydrocarbon having a boiling point of from 30° to 300° C. which is selected from the group consisting of a straight-chain paraffin, an isoparaffin and a cycloparaffin.

13. The method as claimed in claim 11, wherein said oxyisobutyric acid ester is selected from the group consisting of methyl α-methoxyisobutyrate, ethyl α-methoxyisobutyrate, methyl α-ethoxyisobutyrate, ethyl β-ethoxyisobutyrate, methyl β-methoxyisobutyrate, ethyl β-methoxyisobutyrate, methyl β-ethoxyisobutyrate, ethyl β-ethoxyisobutyrate, methyl β-isopropoxyisobutyrate, ethyl β-isopropoxyisobutyrate, isopropyl-β-isopropoxyisobutyrate, butyl β-isopropoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, isopropyl α-hydroxyisobutyrate, and butyl α-hydroxyisobutyrate.

14. The method as claimed in claim 11, wherein said oxyisobutyric acid ester has an acid content of from 0.0001 to 0.5% by weight.

15. A method for removing flux from a surface which comprises administering to a surface in need of such treatment an effective amount of a solvent composition comprising, as an active component, at least 5% by weight of at least one oxyisobutyric acid ester, wherein said oxyisobutyric acid ester is selected from the group consisting of an alkyl α-alkoxyisobutyrate represented by formula (I):

(I)

an alkyl β-alkoxyisobutyrate represented by formula (II):

and an alkyl α-hydroxyisobutyrate represented by formula (III):

wherein $R^1$ and $R^2$ each represent an alkyl group having from 1 to 4 carbon atoms.

16. A method as claimed in claim 15, wherein said composition further comprises at least one compound selected from the group consisting of water, methyl isobutyl carbinol, hexanol, heptanol, octanol, nonanol, 3-methylbutanol, propylene glycol, 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, tripropylene glycol monomethyl ether, tripropylene glycol monopropyl ether, tripropylene glycol monobutyl ether, propylene glycol dimethyl ether, dipropylene glycol dimethyl ether, tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone, methyl isoamyl ketone acetophenone, propiophenone, benzophenone, cyclohexanone, isophorone, pyrrolidone, N-methylpyrrolidone, dimethylformamide, dimethylacetamide, dimethyl sulfoxide, sulfolane, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, methyl propionate, ethyl propionate, butyl propionate benzyl propionate, methyl benzoate, ethyl benzoate, propyl benzoate, diethyl ether, dipropyl ether, dibutyl ether, diphenyl ether, benzyl methyl ether, benzyl ethyl ether, anisole, methoxytoluene, tetrahydrofuran, benzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol, methyl acetoacetate, ethyl acetoacetate, dimethyl maleate, dimethyl malonate, dimethyl succinate, dimethyl glutarate, dimethyl adipate, dimethyl phthalate, toluene, xylene, tetralin, decalin, limonene, and an aliphatic hydrocarbon having a boiling point of from 30° to 300° C. which is selected from the group consisting of a straight-chain paraffin, an isoparaffin and a cycloparaffin.

17. The method as claimed in claim 15, wherein said oxyisobutyric acid ester is selected from the group consisting of methyl α-methoxyisobutyrate, ethyl methoxyisobutyrate, methyl α-ethoxyisobutyrate, ethyl α-ethoxyisobutyrate, methyl β-methoxyisobutyrate, ethyl β-methoxyisobutyrate, methyl β-ethoxyisobutyrate, ethyl β-ethoxyisobutyrate, methyl β-isopropoxyisobutyrate, ethyl β-isopropoxyisobutyrate, isopropyl β-isopropoxyisobutyrate, butyl β-isopropoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, isopropyl α-hydroxyisobutyrate, and butyl α-hydroxyisobutyrate.

18. The method as claimed in claim 15, wherein said oxyisobutyric acid ester has an acid content of from 0.0001 to 0.5% by weight.

19. A method for cleaning a liquid crystal cell which comprises administering to a liquid crystal cell in need of such cleaning an effective amount of a solvent composition comprising, as an active component, at least 5% by weight of at least one oxyisobutyric acid ester, wherein said oxyisobutyric acid ester is selected from the group

consisting of an alkyl α-alkoxyisobutyrate represented by formula (I):

an alkyl β-alkoxyisobutyrate represented by formula (II):

and an alkyl α-hydroxyisobutyrate represented by formula (III):

wherein $R^1$ and $R^2$ each represent an alkyl group having from 1 to 4 carbon atoms.

20. A method as claimed in claim 19, wherein said composition further comprises at least one compound selected from the group consisting of water, heptanol, octanol, nonanol, 3-methylbutanol, propylene glycol, 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, tripropylene glycol monomethyl ether, tripropylene glycol monopropyl ether, propylene glycol dimethyl ether, dipropylene glycol dimethyl ether, tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone, methyl isoamyl ketone, acetophenone, propiophenone, benzophenone, cyclohexanone, pyrrolidone, N-methylpyrrolidone, dimethylformamide, dimethylacetamide, dimethyl sulfoxide, sulfolane, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, methyl propionate, ethyl propionate, butyl propionate, benzyl propionate, methyl benzoate, ethyl benzoate, propyl benzoate, diethyl ether, dipropyl ether, dibutyl ether, diphenyl ether, benzyl methyl ether, benzyl ethyl ether, anisole, phenetole, butyl phenyl ether, methoxytoluene, tetrahydrofuran, dibenzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol, methyl acetoacetate, ethyl acetoacetate, dimethyl maleate, dimethyl malonate, dimethyl succinate, dimethyl glutarate, dimethyl adipate, dimethyl phthalate, methyl cinnamate, ethyl cinnamate, toluene, xylene, tetralin, decalin, limonene, and an aliphatic hydrocarbon having a boiling point of from 30° to 300° C. which is selected from the group consisting of a straight-chain paraffin, an isoparaffin and a cycloparaffin.

21. The method as claimed in claim 19, wherein said oxyisobutyric acid ester is selected from the group consisting of methyl α-methoxyisobutyrate, ethyl α-methoxyisobutyrate, methyl α-ethoxyisobutyrate, ethyl α-ethoxyisobutyrate, methyl β-methoxyisobutyrate, ethyl β-methoxyisobutyrate, methyl β-ethoxyisobutyrate, ethyl β-ethoxyisobutyrate, methyl β-isopropoxyisobutyrate, ethyl β-isopropoxyisobutyrate, isopropyl β-isopropoxyisobutyrate, butyl β-isopropoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, isopropyl α-hydroxyisobutyrate, and butyl α-hydroxyisobutyrate.

22. The method as claimed in claim 19, wherein said oxyisobutyric acid ester has an acid content of from 0.0001 to 0.5% by weight.

23. A method for removing resist on a surface which comprises administering to a surface in need of such treatment an effective amount of a solvent composition comprising, as an active component, at least 5% by weight of at least one oxyisobutyric acid ester, wherein said oxyisobutyric acid aster is selected from the group consisting of an alkyl α-alkoxyisobutyrate represented by formula (I):

$$(CH_3)_2CCO_2R^2 \quad \overset{OR^1}{|} \quad (I)$$

an alkyl β-alkoxyisobutyrate represented by formula (II):

$$R^1OCH_2CHCO_2R^2 \quad \overset{CH_3}{|} \quad (II)$$

and an alkyl α-hydroxyisobutyrate represented by formula (III):

$$(CH_3)_2CCO_2R^2 \quad \overset{OH}{|} \quad (III)$$

wherein $R^1$ and $R^2$ each represent an alkyl group having from 1 to 4 carbon atoms.

24. A method as claimed in claim 23, wherein said composition further comprises at least one compound selected from the group consisting of water, methyl isobutyl carbinol, heptanol, octanol, 3-methylbutanol, propylene glycol, 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, tripropylene glycol monomethyl ether tripropylene glycol monopropyl ether, tripropylene glycol monobutyl ether, propylene glycol dimethyl ether, dipropylene glycol dimethyl ether, tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone, methyl isoamyl ketone, acetophenone, propiophenone, bezophenone, cyclohexanone, pyrrolidone, N-methylpyrrolidone, dimethylformamide, dimethylacetamide, dimethyl sulfoxide, sulfolane, methyl acetate, ethyl acetate, butyl acetate, amyl acetate, 3-methoxybutyl acetate, 3-methyl-3-methoxybutyl acetate methyl lactate ethyl lactate butyl lactate methyl, 3-methoxypropionate, ethyl 3-ethoxypropionate, 2-ethylhexyl acetate, cyclohexyl acetate, benzyl acetate, methyl propionate, ethyl propionate, butyl propionate, benzyl propionate, methyl benzoate, ethyl benzoate, propyl benzoate, isoamyl benzoate, benzyl benzoate, diethyl ether, dipropyl ether, dibutyl ether, diphenyl ether, benzyl methyl ether, benzyl ethyl ether, anisole, phenetole, butyl phenyl ether, methoxytoluene, tetrahydrofuran, dibenzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol, methyl acetoacetate, ethyl acetoacetate, dimethyl maleate, dimethyl malonate, dimethyl succinate, dimethyl glutarate, dimethyl adipate, dimethyl phthalate, toluene, xylene, tetralin, limonene, and an aliphatic hydrocarbon having a boiling point of from 30° to 300° C. which is selected from the group consisting of a straight-chain paraffin, an isoparaffin and a cycloparaffin.

25. The method as claimed in claim 23, wherein said oxyisobutyric acid ester is selected from the group consisting of methyl α-methoxyisobutyrate, ethyl α-methoxyisobutyrate, methyl α-ethoxyisobutyrate, ethyl α-ethoxyisobutyrate, methyl β-methoxyisobutyrate, ethyl β-methoxyisobutyrate, methyl β-ethoxyisobutyrate, ethyl β-ethoxyisobutyrate, methyl β-isopropoxyisobutyrate, ethyl β-isopropoxyisobutyrate, isopropyl β-isopropoxyisobutyrate, butyl β-isopropoxyisobutyrate, methyl β-butoxyisobutyrate, ethyl β-butoxyisobutyrate, butyl β-butoxyisobutyrate, methyl α-hydroxyisobutyrate, ethyl α-hydroxyisobutyrate, isopropyl α-hydroxyisobutyrate, and butyl α-hydroxyisobutyrate.

26. The method as claimed in claim 22, wherein said oxyisobutyric acid ester has an acid content of from 0.0001 to 0.5% by weight.

* * * * *

REEXAMINATION CERTIFICATE (4123rd)

United States Patent
Takayanagi et al.

[11] B1 5,612,303
[45] Certificate Issued: Jul. 18, 2000

[54] SOLVENT COMPOSITION

[75] Inventors: Yasuyuki Takayanagi; Satoshi Endou; Naoki Sugama, all of Kanagawa, Japan

[73] Assignee: Nitto Chemical Industry Co., Ltd., Tokyo, Japan

Reexamination Request:
No. 90/005,309, Mar. 30, 1999

Reexamination Certificate for:
Patent No.: 5,612,303
Issued: Mar. 18, 1997
Appl. No.: 08/555,309
Filed: Nov. 8, 1995

Related U.S. Application Data

[63] Continuation-in-part of application No. 08/260,741, Jun. 15, 1994, abandoned.

[30] Foreign Application Priority Data

| | | | |
|---|---|---|---|
| Jun. 15, 1993 | [JP] | Japan | 5-167374 |
| Jun. 22, 1993 | [JP] | Japan | 5-173606 |
| Sep. 17, 1993 | [JP] | Japan | 5-253688 |
| Dec. 24, 1993 | [JP] | Japan | 5-346056 |
| Mar. 11, 1994 | [JP] | Japan | 6-103457 |

[51] Int. Cl.$^7$ ............... C11D 7/26; C11D 7/50; C11D 7/22

[52] U.S. Cl. ............ 510/174; 510/175; 510/176; 510/243; 510/245; 510/364; 510/365; 510/407; 134/40; 134/42

[58] Field of Search ................. 510/174, 175, 510/176, 243, 245, 364, 365, 407; 134/40, 42

[56] References Cited

U.S. PATENT DOCUMENTS

| | | |
|---|---|---|
| 5,116,426 | 5/1992 | Asano et al. |
| 5,215,857 | 6/1993 | Hosaka et al. ............ 430/191 |

OTHER PUBLICATIONS

Hawley's Condensed Chemical Dictionary, 11th Edition, 1987, pp. 235, 489 and 967.

Corrosion Resistance of Metals and Alloys, Second Edition, 1963, pp. 67, 68 and 69.

*Primary Examiner*—Margaret Einsmann

[57] ABSTRACT

A solvent composition containing at least one of an alkyl α-alkoxyisobutyrate, an alkyl β-alkoxyisobutyrate, and an alkyl α-hydroxyisobutyrate as an active component is disclosed. The solvent composition is of low toxicity and harmless to humans, has an extremely high dissolving power for high polymers, fats and oils, fluxes, liquid crystals, etc., produces no environment destructive substance, gives off no offensive odor, and has a relatively high boiling point indicative of safety and ease in handling.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 15, line 30, after the end of Table 6, insert:

*As can be seen from Table 1, the oxyisobutyric esters of the present invention have compatibility equal or superior to the conventional general-purpose solvents, such as ECA, and thus can be used as a mixture with a broad range of other solvents.*

*As can be seen from Tables 2 and 3, the rate of evaporation can arbitrarily be selected by a proper choice of the ester group. The rate of evaporation of the oxyisobutyric esters of the present invention is about 2 to 3 times as high as that of ECA or ethyl lactate, which have been widely used, proving that the oxyisobutyric esters provide a solvent system having good volatility.*

*As can be seen from Tables 4, 5 and 6, the oxyisobutyric esters of the present invention need a shorter time for dissolving various resins, often used in coating compositions and adhesives, than needed by the conventional general-purpose solvents. This reveals their excellent resin-dissolving power.*

EXAMPLE 5

*A 50 mm long, 20 mm wide, and 2 mm thick stainless steel plate with its surface polished was uniformly coated with commercially available fats and oils, i.e., cutting oil (Daphne-Mag plus LA15, a product of Idemitsu Kosan Co., Ltd.), press oil (Unipress DP120, a product of Nippon Oil Co., Ltd.) or grease (Albania Grease 1, a product of Showa Shell Sekiyu K.K.). One hour later, the coated plate was put in a washing bottle containing the degreasing agent shown in Table 7 below, and the bottle and content was shaken at 40° C. for 5 minutes. The stainless steel plate was taken out and dried in hot air. The oil or grease remaining on the plate was observed with the naked eye and under a metallurgical microscope, and the degreasing power was evaluated according to the following rating system.*

*A ... No residual oil or grease was observed with the naked eye or under a metallurgical microscope.*

*B ... Residual oil or grease was not observed with the naked eye, but observed under a metallurgical microscope.*

*C ... Residual oil or grease was observed with the naked eye.*

*The results obtained are shown in Table 7 below.*

Column 26, lines 24–52:

TABLE 19

| Storage Time | Item of Analysis and Observation | Example 11 | | Comparative Example 11 | |
|---|---|---|---|---|---|
| Initial | Ester [parity] *purity* (wt %) | 99.6 | 99.3 | 99.1 | 99.0 |
| | *Acid content (wt %):* | | | | |
| | Sulfuric acid | 0.062 | — | 0.45 | — |
| | Acetic acid | — | 0.30 | — | 0.61 |
| | Methacrylic acid | *0.023* | *0.05* | *0.18* | *0.20* |
| | Total | 0.085 | 0.35 | 0.63 | 0.81 |
| | Appearance of ester | colorless and transparent | colorless and transparent | colorless and transparent | colorless and transparent |
| 3 Mts. | Ester [parity] *purity* (wt. %) | 99.6 | 99.3 | 98.6 | 99.1 |
| | Appearance of ester | no change | no change | no change | pale yellow |
| | Appearance of drum | no change | no change | no change | black specks |
| 6 Mts. | Ester [parity] *purity* (wt. %) | 99.6 | 99.2 | 97.5 | 96.8 |
| | Appearance of ester | no change | no change | no change | pale yellow |
| | Appearance of drum | no change | no change | no change | black specks |
| 9 Mts. | Ester [parity] *purity* (wt. %) | 99.5 | 99.2 | 96.0 | 94.7 |
| | Appearance of ester | no change | no change | pale yellow | yellow |
| | Appearance of drum | no change | no change | black specks | almost all over blackened |
| 12 Mts. | Ester purity (wt. %) | 99.5 | 99.1 | 94.1 | 92.0 |
| | Appearance of ester | no change | no change | yellow | dark yellow |
| | Appearance of drum | no change | no change | black specks | all over Blackened |

Column 27, lines 1–26:

TABLE 20

| Storage Time | Item of Analysis and Observation | Example 12 | | Comparative Example 12 | |
|---|---|---|---|---|---|
| Initial | Ester [parity] *purity* (wt %) | 99.77 | 99.51 | 99.19 | 98.96 |
| | Acid content (wt %): | | | | |
| | Sulfuric acid | 0.05 | — | 0.45 | — |
| | α-Hydroxyisobutric acid | *0.02* | *0.06* | *0.18* | *0.72* |
| | Total | 0.07 | 0.06 | 0.63 | 0.72 |
| | Appearance of ester | colorless and transparent | colorless and transparent | colorless and transparent | colorless and transparent |
| 3 Mts. | Ester [parity] *purity* (wt. %) | 99.71 | 99.37 | 98.74 | 98.49 |
| | Appearance of ester | no change | no change | no change | pale yellow |
| | Appearance of drum | no change | no change | no change | black specks |
| 6 Mts. | Ester [parity] *purity* (wt. %) | 99.70 | 99.29 | 97.28 | 96.75 |
| | Appearance of ester | no change | no change | pale yellow | pale yellow |
| | Appearance of drum | no change | no change | no change | black specs |
| 9 Mts. | Ester [parity] *purity* (wt. %) | 99.62 | 99.23 | 95.81 | 94.61 |
| | Appearance of ester | no change | no change | pale yellow | yellow |
| | Appearance of drum | no change | no change | black specks | almost all over blackened |
| 12 Mts. | Ester purity (wt. %) | 99.46 | 99.15 | 93.27 | 92.08 |
| | Appearance of ester | no change | no change | yellow | dark yellow |
| | Appearance of drum | no change | no change | black specks | all over Blackened |

AS A RESULT OF REEXAMINATION, IT HAS BEEN DETERMINED THAT:

Claim 2 is cancelled.

Claims 1, 4, 7, 8, 11, 12, 15, 16, 19, 23 and 26 are determined to be patentable as amended.

Claims 3, 5, 6, 9–10, 13, 14, 17, 18, 20–22, 24 and 25, dependent on an amended claim, are determined to be patentable.

New claims 27–35 are added and determined to be patentable.

1. A method for dissolving a polymeric compound which comprises administering to the polymeric compound in need of such treatment an effective amount of a solvent composition comprising, as an active component, at least 5% by weight of at least one oxyisobutyric acid ester, *wherein said solvent composition does not contain a halogen solvent,* wherein said oxyisobutyric acid ester is selected from the group consisting of an alkyl α-alkoxyisobutyrate represented by formula (I):

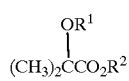
(I)

an alkyl β-alkoxyisobutyrate represented by formula (II):

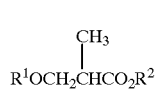
(II)

and an alkyl α-hydroxyisobutyrate represented by formula (III):

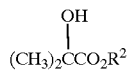
(III)

wherein $R^1$ and $R^2$ each represent an alkyl group having from 1 to 4 carbon atoms; *and wherein said polymeric compound is selected from the group consisting of epoxy resins, acrylic resins, vinyl acetate resins, vinyl chloride resins, alkyd resins, polyester resins, unsubstituted polystyrene resins, phenoxy resins, polysulfone, methyl methacrylate-styrene copolymer, acrylonitrile-styrene copolymer and general hydrocarbon-based fats.*

4. A method as claimed claim 1, wherein said composition further comprises at least one compound selected from the group consisting of water, methyl isobutyl carbinol, hexanol, heptanol, octanol, nonanol, 3-methylbutanol, propylene glycol[;], 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, tripropylene glycol monoethyl ether, tripropylene glycol [monobutyl] *monopropyl* ether, tripropylene glycol monobutyl ether, propylene glycol dimethyl ether, [dipropylane] *dipropylene* glycol dimethyl ether, tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone, methyl isoamyl ketone, acetophenone, propiophenone, benzophenone, cyclohexanone, isophorone, pyrrolidone, N-methylpyrrolidone, dimethylformamide, dimethylacetamide, dimethyl sulfoxide, sulfolane, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, methyl propionate, ethyl propionate, butyl propionate, benzyl propionate, methyl benzoate, ethyl benzoate, propyl benzoate, isoamyl benzoate, benzyl benzoate, diethyl ether [dibutyl] *dipropyl* ether, dibutyl ether, diphenyl ether, benzyl methyl ether, benzyl ethyl ether, anisole, phenetole, butyl phenyl ether, methoxytoluene, tetrahydrofuran, dibenzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol methyl acetoacetate, ethyl acetoacetate, dimethyl maleate, *dimethyl* malonate, [dimethyl succinate,] dimethyl succinate, dimethyl glutarate, dimethyl adipate, dimethyl phthalate, methyl cinnamate, ethyl cinnamate, toluene, xylene, tetralin, decalin, limonene, and an aliphatic hydrocarbon having a boiling point of from 30° to 300° C., which is selected from the group consisting of a straight-chain paraffin, an isoparaffin and a cycloparaffin.

7. A method for removing fats and oils on a surface which comprises administering to *a* surface in need of such treatment an effective amount of a solvent composition comprising, as an active component, at least 10% by weight of at least one oxyisobutyric acid ester, *wherein said solvent composition does not contain a halogen solvent and* wherein said oxyisobutyric acid ester as selected from the group consisting of an alkyl α-alkoxyisobutyrate represented by formula (I):

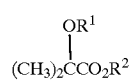

an alkyl β-alkoxyisobutyrate represented by formula (II):

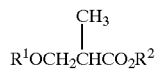

and an alkyl α-hydroxyisobutyrate represented by formula (III):

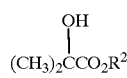

wherein $R^1$ and $R^2$ each represent an alkyl group having from 1 to 4 carbon atoms.

8. A method as claimed in claim 7, wherein said composition further comprises at least one compound selected from the group consisting of water, hexanol, heptanol, octanol, 3-methylbutanol, propylene glycol, 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, tripropylene glycol monomethyl ether, tripropylene glycol monopropyl ether, propylene glycol dimethyl ether, dipropylene glycol dimethyl ether, tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone, methyl isoamyl ketone, acetophenone, propiophenone, benzophenone, cyclohexanone isophorone, pyrrolidone, N-methypyrrolidone, dimethylformamide, dimethylacetamide, dimethyl sulfoxide, sulfolane, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, methyl propionate, ethyl propionate, butyl propionate, benzyl propionate, methyl benzoate, ethyl benzoate, propyl benzoate, isoamyl benzoate, benzyl benzoate, diethyl ether, dipropyl ether, dibutyl ether, diphenyl ether, benzyl methyl ether, benzyl ethyl ether, anisole, phenetole, butyl phenyl ether, methoxytoluene, tetrahydrofuran, dibenzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol, methyl acetoacetate, ethyl acetoacetate, dimethyl maleate, dimethyl malonate, dimethyl succinate, dimethyl glutarate, dimethyl adipate, dimethyl phthalate, toluene, xylene, tetralin, decalin, limonene, and an aliphatic hydrocarbon having a boiling point of from 30° to 300° C. which is selected from the group consisting of a straight-chain paraffin, an isoparaffin and a cycloparaffin.

11. A method for removing ink from a surface which comprises administering to a surface in need of such treatment an effective amount of a solvent composition comprising, as an active component, at least 5% by weight of at least one oxyisobutyric acid ester, *wherein said solvent composition does not contain a halogen solvent and* wherein said oxyisobutyric acid ester is selected from the group consisting of an alkyl α-alkoxyisobutyrate represented by formula (I):

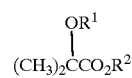

an alkyl β-alkoxyisobutyrate represented by formula (II):

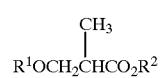

and an alkyl α-hydroxyisobutyrate represented by formula (III):

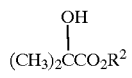

wherein $R^1$ and $R^2$ each represent an alkyl group having from 1 to 4 carbon atoms.

12. A method as claimed in claim 11, wherein said composition further comprises at least one compound selected from the group consisting of water, methyl isobutyl carbinol, octanol, nonanol, 3-methylbutanol, propylene glycol, 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, tripropylene glycol monomethyl ether, tripropylene glycol monopropyl ether, tripropylene glycol monobutyl ether, propylene glycol dimethyl ether, dipropylene glycol dimethyl ether, tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone, methyl isoamyl ketone, acetophenone, propiophenone, benzophenone, cyclohexanone, isophorone, pyrrolidone, N-methypyrrolidone, dimethylformamide, dimethylacetamide, dimethyl sulfoxide, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, methyl propionate, ethyl propionate, butyl propionate, benzyl propionate, methyl benzoate, ethyl benzoate, propyl benzoate, isoamyl benzoate, benzyl benzoate, diethyl ether, dipropyl ether, dibutyl ether, diphenyl ether, benzyl methyl ether, benzyl ethyl [ester] *ether*, anisole, phenetole, butyl phenyl ether, methoxytoluene, tetrahydrofuran, dibenzyl ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol, methyl[,] acetoacetate, ethyl acetoacetate, dimethyl maleate, dimethyl malonate, dimethyl succinate, dimethyl glutarate, dimethyl adipate, dimethyl phthalate, methyl cinnamate, ethyl cinnamate, toluene, xylene, tetralin, limonene, and an aliphatic hydrocarbon having a boiling point of from 30° to 300° C. which is selected from the group consisting of a straight-chain paraffin, an isoparaffin and a cycloparaffin.

15. A method for removing flux from a surface which comprises administering to a surface in need of such treatment an effective amount of a solvent composition comprising, as an active component, at least 5% by weight of at least one oxyisobutyric acid ester, *wherein said solvent composition does not contain a halogen solvent and* wherein said oxyisobutyric acid ester is selected from the group consisting of an alkyl α-alkoxyisobutyrate represented by formula (I):

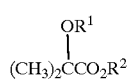

(I)

an alkyl β-alkoxyisobutyrate represented by formula (II):

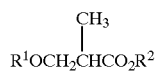

(II)

and an alkyl α-hydroxyisobutyrate represented by formula (III):

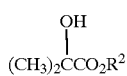

(III)

wherein $R^1$ and $R^2$ each represent an alkyl group having from 1 to 4 carbon atoms.

16. A method as claimed in claim 15, wherein said composition further comprises at least one compound selected from the group consisting of water, methyl isobutyl carbinol, hexanol, heptanol, octanol, nonanol, 3-methylbutanol, propylene glycol, 3-methoxybutanol, 3-methyl-3-methoxybutanol, propylene glycol monomethyl ether, propylene glycol monopropyl ether, propylene glycol monobutyl ether, dipropylene glycol monomethyl ether, dipropylene glycol monopropyl ether, dipropylene glycol monobutyl ether, tripropylene glycol monomethyl ether, tripropylene glycol monopropyl ether, tripropylene glycol monobutyl ether, propylene glycol dimethyl ether, dipropylene glycol dimethyl ether, tripropylene glycol dimethyl ether, 3,5,5-trimethyl-1-hexanol, 2-ethyl-1-hexanol, cyclohexanol, benzyl alcohol, acetone, methyl ethyl ketone, methyl isobutyl ketone, methyl isoamyl ketone, acetophenone, propiophenone, benzophenone, cyclohexanone, isophorone, pyrrolidone, N-methypyrrolidone, dimethylformamide, dimethylacetamide, dimethyl sulfoxide, sulfolane, methyl acetate, ethyl acetate, butyl acetate, amyl acetate, 3-methoxybutyl acetate, 3-methyl-3-methoxybutyl acetate, methyl lactate, ethyl lactate, butyl lactate, methyl 3-methoxypropionate, ethyl 3-ethoxypropionate, 2-ethylhexyl acetate, cyclohexyl acetate, benzyl acetate, methyl propionate, ethyl propionate, butyl propionate, benzyl propionate, methyl benzoate, ethyl benzoate, propyl benzoate, diethyl ether, dipropyl ether, dibutyl ether, diphenyl ether, benzyl methyl ether, benzyl ethyl ether, anisole, methoxytoluene, tetrahydrofuran, [benzyl] *dibenzyl* ether, acetonitrile, γ-butyrolactone, propylene carbonate, propylene glycol monomethyl ether acetate, propylene glycol monomethyl ether propionate, dipropylene glycol monomethyl ether acetate, propylene glycol diacetate, diacetone alcohol, methyl acetoacetate, ethyl acetoacetate, dimethyl maleate, dimethyl malonate, dimethyl succinate, dimethyl glutarate, dimethyl adipate, dimethyl phthalate, toluene, xylene, tetralin, decalin, limonene, and an aliphatic hydrocarbon having a boiling point of from 30° to 300° C. which is selected from the group consisting of a straight-chain paraffin, an isoparaffin and a cycloparaffin.

19. A method for cleaning a liquid crystal cell which comprises administering to a liquid crystal cell in need of such cleaning an effective amount of a solvent composition comprising, as an active component, at least 5% by weight of at least one oxyisobutyric acid ester, *wherein said solvent composition does not contain a halogen solvent and* wherein said oxyisobutyric acid ester is selected from the group consisting of an alkyl α-alkoxyisobutyrate represented by formula (I):

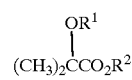

(I)

an alkyl β-alkoxyisobutyrate represented by formula (II):

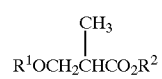

(II)

and an alkyl α-hydroxyisobutyrate represented by formula (III):

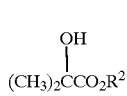

(III)

wherein $R^1$ and $R^2$ each represent an alkyl group having from 1 to 4 carbon atoms.

23. A method for removing resist on a surface which comprises administering to a surface in need of such treatment an effective amount of a solvent composition comprising, as an active component, at least 5% by weight of at least one oxyisobutyric acid ester, *wherein said solvent composition does not contain a halogen solvent and* wherein said oxyisobutyric acid ester is selected from the group consisting of an alkyl α-alkoxyisobutyrate represented by formula (I):

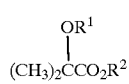

(I)

an alkyl β-alkoxyisobutyrate represented by formula (II):

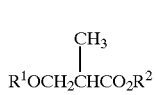

(II)

and an alkyl α-hydroxyisobutyrate represented by formula (III):

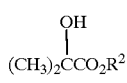

(III)

wherein $R^1$ and $R^2$ each represent an alkyl group having from 1 to 4 carbon atoms.

26. The method as claimed in claim [22] *23*, wherein said oxyisobutyric acid ester has an acid content of from 0.0001 to 0.5% by weight.

27. *A method for dissolving a polymeric compound which comprises administering to the polymeric compound in need of such treatment an effective amount of a solvent composition comprising, as an active component, at least 5% by weight of at least one oxyisobutyric acid ester, wherein said oxyisobutyric acid ester is selected from the group consisting of an alkyl α-alkoxyisobutyrate represented by formula*

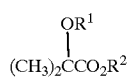

(I)

*an alkyl β-alkoxyisobutyrate represented by formula (II):*

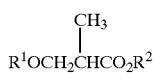

(II)

*and an alkyl α-hydroxyisobutyrate represented by formula (III):*

(III)

*wherein $R^1$ and $R^2$ each represent an alkyl group having from 1 to 4 carbon atoms; and wherein said polymeric compound is a natural resin.*

28. *The method as claimed in claim 23, wherein the material of said resist is selected from the group consisting of cyclized rubber, polysilicic acid, (meth)acrylic resins and (meth)acrylic acid copolymers.*

29. *The method as claimed in claim 4, wherein said solvent composition consists of said at least one oxyisobutyric acid ester and said at least one compound.*

30. *The method as claimed in claim 8, wherein said solvent composition consists of said at least one oxyisobutyric acid ester and said at least one compound.*

31. *The method as claimed in claim 12, wherein said solvent composition consists of said at least one oxyisobutyric acid ester and said at least one compound.*

32. *The method as claimed in claim 16, wherein said solvent composition consists of said at least one oxyisobutyric acid ester and said at least one compound.*

33. *The method as claimed in claim 20, wherein said solvent composition consists of said at least one oxyisobutyric acid ester and said at least one compound.*

34. *The method as claimed in claim 24, wherein said solvent composition consists of said at least one oxyisobutyric aicd ester and said at least one compound.*

35. *A method for dissolving a polymeric compound which comprises administering to the polymeric compound in need of such treatment an effective amount of a solvent composition comprising, as an active component, at least 5% by weight of at least one oxyisobutyric acid ester, wherein said oxyisobutyric acid ester is selected from the group consisting of an alkyl α-alkoxyisobutyrate represented by formula*

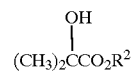

(I)

*an alkyl β-alkoxyisobutyrate represented by formula (II):*

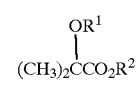

(II)

*and an alkyl α-hydroxyisobutyrate represented by formula (III):*

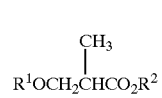

(III)

*wherein $R^1$ and $R^2$ each represent an alkyl group having from 1 to 4 carbon atoms; and wherein said polymeric compound is a cellulose resin.*

\* \* \* \* \*